(12) United States Patent
Karles

(10) Patent No.: US 10,405,580 B2
(45) Date of Patent: Sep. 10, 2019

(54) MECHANICALLY-ADJUSTABLE E-VAPING DEVICE FLAVOR ASSEMBLY

(71) Applicant: Altria Client Services LLC, Richmond, VA (US)

(72) Inventor: Georgios Karles, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 455 days.

(21) Appl. No.: 15/204,263

(22) Filed: Jul. 7, 2016

(65) Prior Publication Data

US 2018/0007965 A1 Jan. 11, 2018

(51) Int. Cl.
*A61M 15/06* (2006.01)
*A24F 47/00* (2006.01)
(Continued)

(52) U.S. Cl.
CPC ............ *A24F 47/008* (2013.01); *A24B 15/16* (2013.01); *A61M 11/042* (2014.02);
(Continued)

(58) Field of Classification Search
None
See application file for complete search history.

(56) References Cited

U.S. PATENT DOCUMENTS 3,948,445 A * 4/1976 Andeweg ............ A01M 1/2066
239/53
5,038,394 A * 8/1991 Hasegawa ........... A01M 1/2077
392/392
(Continued)

FOREIGN PATENT DOCUMENTS

| EP | 2740371 A1 | 6/2014 |
|---|---|---|
| WO | WO-2010/145805 A1 | 12/2010 |
| WO | WO-2014/132045 A2 | 9/2014 |
| WO | WO-2015/038981 A2 | 3/2015 |
| WO | WO-2015/052192 A1 | 4/2015 |
| WO | WO-2016/069903 A1 | 5/2016 |

OTHER PUBLICATIONS

International Search Report and Written Opinion for Appliation No. PCT/EP2017/067163 dated Oct. 2, 2017.

*Primary Examiner* — Thor S Campbell
(74) *Attorney, Agent, or Firm* — Harness, Dickey & Pierce, P.L.C.

(57) ABSTRACT

A flavor assembly for an e-vaping device cartridge is configured to provide mechanically-adjustable flavorant elution to form a flavored vapor. The flavor assembly may include at least one flavor material holding a flavorant and a exposure control mechanism configured to adjustably expose the at least one flavor material to the vaporizer assembly to adjustably control flavorant elution from the at least one flavor reservoir into the generated vapor. The flavor assembly may be included in a flavor assembly module. The flavor assembly module may include an interface configured to couple with a vaporizer assembly and direct generated vapors formed by the vaporizer assembly to the flavor assembly. The flavor assembly may include multiple flavor materials holding different flavorants. The exposure control mechanism may adjustably expose a selected flavor material. The flavor assembly may be included in an e-vaping device that includes control circuitry configured to control the exposure control mechanism.

12 Claims, 11 Drawing Sheets

(51) Int. Cl.
*A24B 15/16* (2006.01)
*A61M 11/04* (2006.01)
*A61M 15/00* (2006.01)
*F16K 15/00* (2006.01)

(52) U.S. Cl.
CPC ........ *A61M 15/0003* (2014.02); *A61M 15/06* (2013.01); *F16K 15/00* (2013.01)

(56) References Cited

U.S. PATENT DOCUMENTS

| | | | |
|---|---|---|---|
| 5,479,948 A * | 1/1996 | Counts | A24F 47/008 131/194 |
| 5,695,692 A * | 12/1997 | Kennedy | A61L 9/122 239/60 |
| 6,078,728 A * | 6/2000 | O'Rourke | A01M 1/2077 392/390 |
| 6,285,830 B1 * | 9/2001 | Basaganas Millan | A01M 1/2077 261/DIG. 65 |
| 6,374,044 B1 * | 4/2002 | Freidel | A61L 9/03 239/34 |
| 6,446,583 B2 * | 9/2002 | Vieira | A01M 1/2077 122/366 |
| 6,782,194 B2 * | 8/2004 | Schneiderbauer | A61L 9/037 219/403 |
| 6,996,335 B2 * | 2/2006 | Zobele | A01M 1/2077 392/386 |
| 7,209,650 B2 * | 4/2007 | Caserta | A01M 1/2077 392/387 |
| 7,734,159 B2 * | 6/2010 | Beland | A61L 9/035 392/390 |
| RE44,312 E * | 6/2013 | Vieira | A01M 1/2077 219/486 |
| 9,215,895 B2 | 12/2015 | Bowen et al. | |
| 2003/0007787 A1 * | 1/2003 | Rymer | A01M 1/2077 392/395 |
| 2005/0276583 A1 * | 12/2005 | Hooks | A01M 1/2077 392/395 |
| 2008/0226269 A1 * | 9/2008 | DeWitt | A01M 1/2077 392/386 |
| 2011/0290244 A1 * | 12/2011 | Schennum | A61M 15/06 128/200.23 |
| 2014/0123989 A1 | 5/2014 | LaMothe | |
| 2014/0209105 A1 * | 7/2014 | Sears | F22B 1/28 131/328 |
| 2015/0216237 A1 * | 8/2015 | Wensley | A24F 47/008 131/273 |
| 2015/0223521 A1 | 8/2015 | Menting et al. | |
| 2015/0272220 A1 | 10/2015 | Spinka et al. | |
| 2016/0050975 A1 * | 2/2016 | Worm | A24F 47/008 131/328 |
| 2016/0135506 A1 * | 5/2016 | Sanchez | A24F 47/008 131/329 |
| 2016/0331036 A1 * | 11/2016 | Cameron | H04M 1/7253 |
| 2017/0172215 A1 * | 6/2017 | Li | H05B 3/42 |
| 2017/0340011 A1 * | 11/2017 | Batista | A24F 47/008 |

* cited by examiner

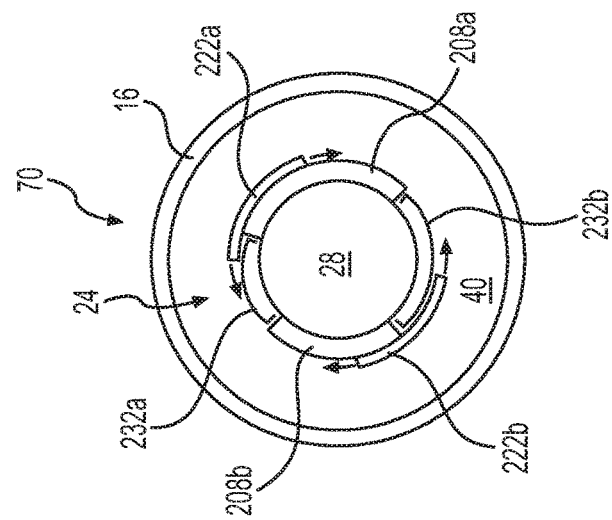
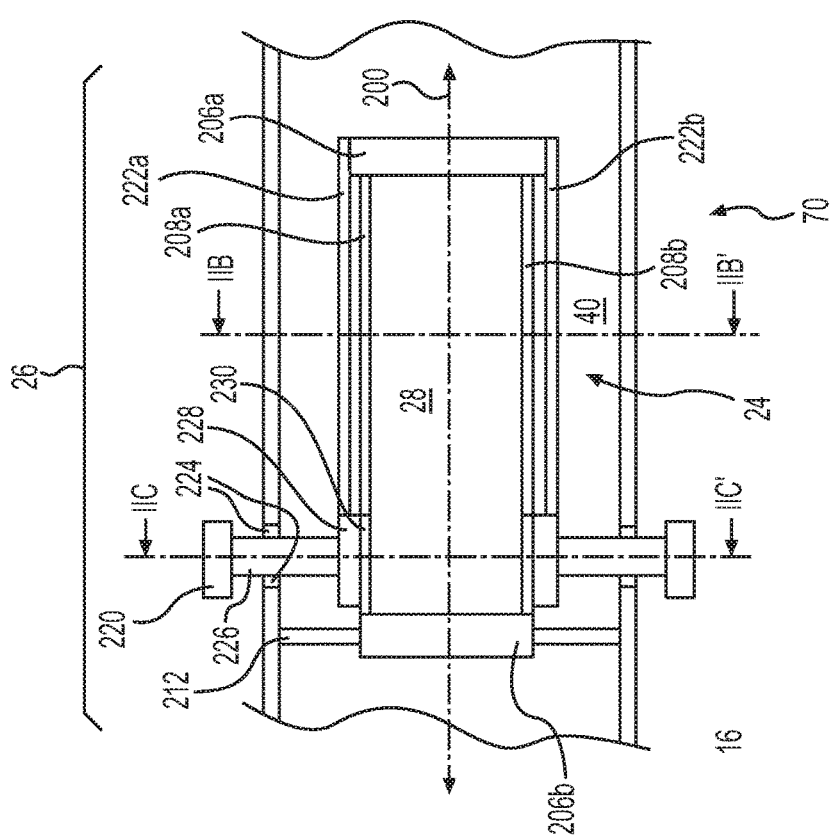
FIG. 2B
FIG. 2A

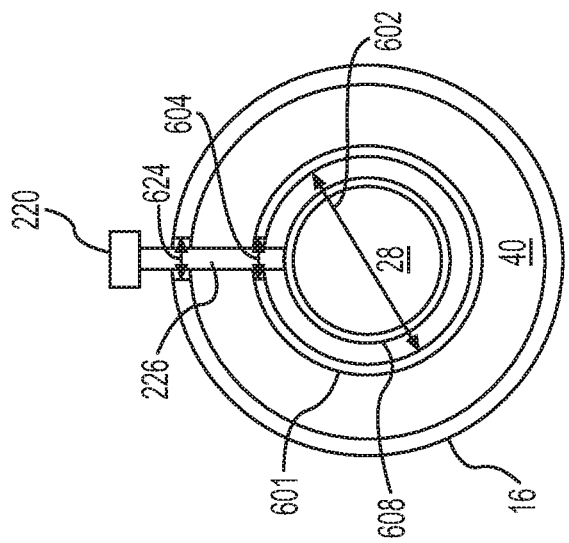
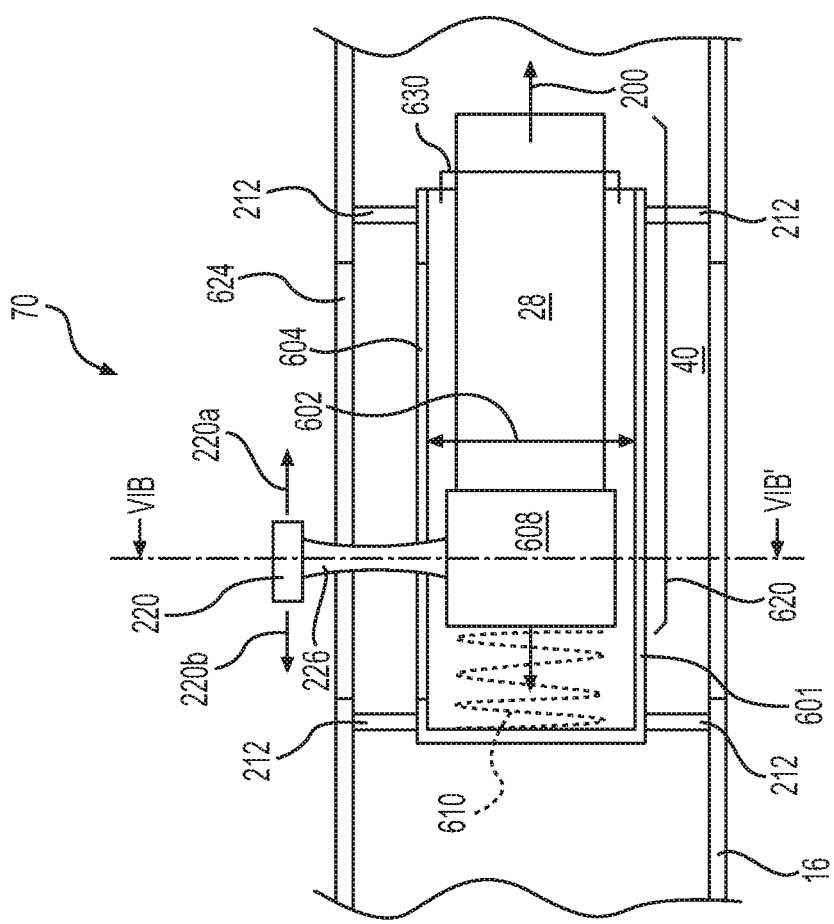
FIG. 6B
FIG. 6A

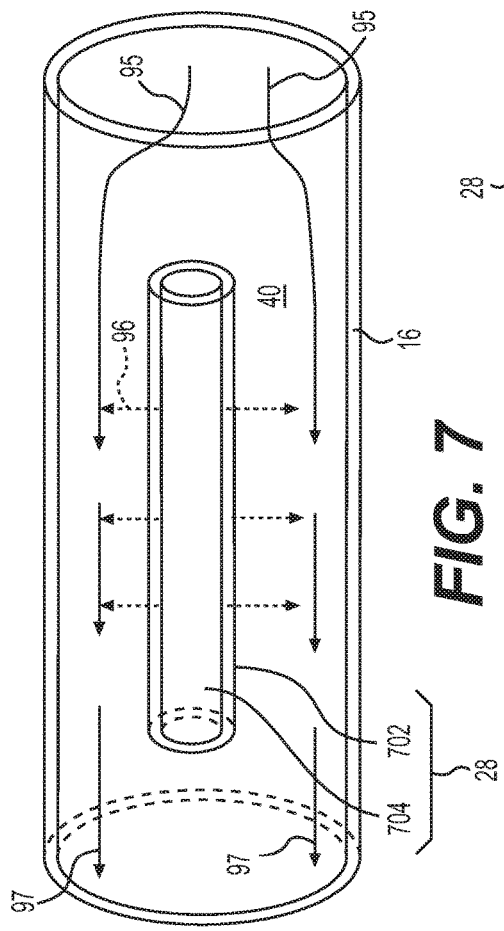
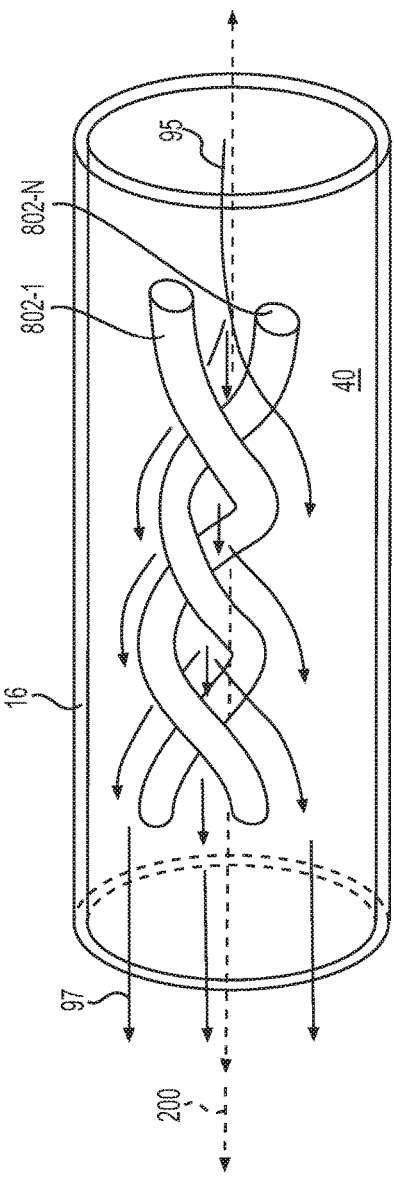

MECHANICALLY-ADJUSTABLE E-VAPING DEVICE FLAVOR ASSEMBLY

BACKGROUND

Field

The present disclosure relates to electronic vaping and e-vaping devices.

Description of Related Art

E-vaping devices, also referred to herein as electronic vaping devices (EVDs) may be used by adult vapers for portable vaping. Flavored vapors within an e-vaping device may be used to deliver a flavor along with the vapor that may be produced by the e-vaping device. The flavored vapors may be delivered via a flavor system.

In some cases, a loss of flavoring in a flavored vapor from a flavor system may occur when the flavor system is exposed to a heat source. In some cases, a loss of flavoring in a flavored vapor may occur as a result of chemical reactions between the flavor system and vapors when the vapors are at a sufficiently high temperature.

Such a loss of flavoring from a flavoring system may reduce a sensory experience provided by an e-vaping device in which the flavoring system is included.

SUMMARY

According to some example embodiments, a cartridge for an electronic vaping device (EVD) may include a vaporizer assembly configured to form a generated vapor; and a flavor assembly coupled to the vaporizer assembly. The flavor assembly may be configured to mechanically control flavorant elution into the generated vapor to form a flavored vapor. The flavor assembly may include at least one flavor material holding a flavorant, and at least one exposure control mechanism configured to adjustably expose the at least one flavor material to the vaporizer assembly to control elution of the flavorant into the generated vapor.

The at least one exposure control mechanism may be configured to adjustably translate the at least one flavor material along a longitudinal axis of the cartridge to adjustably expose the at least one flavor material to the vaporizer assembly.

The at least one exposure control mechanism may include a screw mechanism. The screw mechanism may be configured to adjustably translate the at least one flavor material along the longitudinal axis based on rotation of the screw mechanism around the longitudinal axis.

The at least one exposure control mechanism may include a spring element. The spring element may be configured to exert a spring force on the at least one flavor material to adjustably expose the at least one flavor material to the vaporizer assembly.

The at least one exposure control mechanism may be configured to move a sheath element to adjustably expose the at least one flavor material to the vaporizer assembly.

The at least one exposure control mechanism may be configured to rotate the sheath element around a longitudinal axis of the cartridge to adjustably expose the at least one flavor material to the vaporizer assembly.

The at least one flavor material may include at least one permeation tube enclosing a liquid flavorant, the permeation tube being configured to elute the liquid flavorant to the generated vapor based on permeation of the liquid flavorant through the permeation tube.

The at least one flavor material may be a helix extending around a longitudinal axis of the cartridge.

The flavor assembly may include a plurality of flavor materials. At least two of the flavor materials may hold different flavorants.

The at least one exposure control mechanism may be configured to expose a selected one of the flavor materials to the vaporizer assembly.

The flavor assembly may include a drive motor coupled to the exposure control mechanism, the drive motor being operable to control the exposure control mechanism such that the exposure control mechanism adjustably exposes the flavor material to the vaporizer assembly based on the drive motor.

The at least one flavor material may include at least one botanical substance. The at least one botanical substance may include the at least one flavorant.

According to some example embodiments, an e-vaping device may include a cartridge and a power supply section. The cartridge may include a vaporizer assembly configured to form a generated vapor; and a flavor assembly coupled to the vaporizer assembly. The flavor assembly may be configured to mechanically control flavorant elution into the generated vapor to form a flavored vapor. The flavor assembly may include at least one flavor material holding a flavorant and at least one exposure control mechanism configured to adjustably expose the at least one flavor material to the vaporizer assembly to control elution of the flavorant into the generated vapor. The power supply section may be configured to selectively supply power to the vaporizer assembly.

The e-vaping device may further include control circuitry configured to control the at least one exposure control mechanism to adjustably expose the at least one flavor material to the vaporizer assembly.

The flavor assembly may include a drive motor coupled to the exposure control mechanism. The control circuitry may be configured to adjustably control the drive motor to adjustably control the at least one exposure control mechanism based on controlling the drive motor.

The control circuity may be configured to adjustably expose the at least one flavor material to the vaporizer assembly based on a quantity of generated vapor formed by the vaporizer assembly.

The at least one exposure control mechanism may be configured to translate the at least one flavor material along a longitudinal axis of the cartridge to adjustably expose the at least one flavor material to the vaporizer assembly.

The at least one exposure control mechanism may include a screw mechanism, the screw mechanism being configured to adjustably translate the at least one flavor material along the longitudinal axis based on rotation of the screw mechanism around the longitudinal axis.

The at least one exposure control mechanism may include a spring element, the spring element being configured to exert a spring force on the at least one flavor material to adjustably expose the at least one flavor material to the vaporizer assembly.

The at least one exposure control mechanism may be configured to move a sheath element to adjustably expose the at least one flavor material to the vaporizer assembly.

The at least one exposure control mechanism may be configured to rotate the sheath element around a longitudinal axis of the cartridge to adjustably expose the at least one flavor material to the vaporizer assembly.

The at least one flavor material may include at least one permeation tube enclosing a liquid flavorant. The permeation tube may be configured to elute the liquid flavorant to the generated vapor based on permeation of the liquid flavorant through the permeation tube.

The at least one flavor material may be a helix extending around a longitudinal axis of the cartridge.

The flavor assembly may include a plurality of flavor materials. At least two of the flavor materials may hold different flavorants.

The at least one exposure control mechanism may be configured to expose a selected one of the flavor materials to the vaporizer assembly.

The at least one flavor material may include at least one botanical substance. The at least one botanical substance may include the at least one flavorant.

According to some example embodiments, a flavor assembly module for an electronic vaping device (EVD) may include an interface and a flavor assembly. The flavor assembly may be in fluid communication with the interface. The interface may be configured to removably couple with a vaporizer assembly. The interface may be further configured to direct generated vapor formed by the vaporizer assembly to the flavor assembly. The flavor assembly may be configured to mechanically control flavorant elution into the generated vapor to form a flavored vapor. The flavor assembly may include at least one flavor material holding a flavorant and at least one exposure control mechanism configured to adjustably expose the at least one flavor material to fluid communication with the interface.

The at least one exposure control mechanism may be configured to translate the at least one flavor material along a longitudinal axis of the flavor assembly module to adjustably expose the at least one flavor material to fluid communication with the interface.

The at least one exposure control mechanism may include a screw mechanism. The screw mechanism may be configured to adjustably translate the at least one flavor material along the longitudinal axis based on rotation of the screw mechanism around the longitudinal axis.

The at least one exposure control mechanism may be configured to move a sheath element to adjustably expose the at least one flavor material to fluid communication with the interface.

The at least one exposure control mechanism may be configured to rotate the sheath element around a longitudinal axis of the flavor assembly module to adjustably expose the at least one flavor material to fluid communication with the interface.

The at least one flavor material may include at least one permeation tube enclosing a liquid flavorant. The flavor assembly module may be configured to elute the liquid flavorant from the flavor material based on permeation of the liquid flavorant through the permeation tube.

The at least one flavor material may be a helix extending around a longitudinal axis of the flavor assembly module.

The flavor assembly may include a plurality of flavor materials. At least two of the flavor materials may hold different flavorants.

The at least one exposure control mechanism may be configured to expose a selected one of the flavor materials to fluid communication with the interface.

The at least one flavor material may include at least one botanical substance, the at least one botanical substance including the at least one flavorant.

The flavor assembly may include a drive motor coupled to the exposure control mechanism, the drive motor being operable to control the exposure control mechanism such that the exposure control mechanism adjustably exposes the flavor material to fluid communication with the interface based on the drive motor.

The flavor assembly may include a reservoir configured to hold the flavorant.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 2A is a cross-sectional view of a flavor assembly according to some example embodiments.

FIG. 2B is a cross-sectional view along line IIB-IIB' of the flavor assembly of FIG. 2A.

FIG. 6A is a cross-sectional view of a flavor assembly according to some example embodiments.

FIG. 6B is a cross-sectional view along line VIB-VIB' of the flavor assembly of FIG. 6A.

FIG. 7 is a perspective view of a flavor material according to some example embodiments.

FIG. 8 is a perspective view of a flavor material according to some example embodiments.

DETAILED DESCRIPTION OF EXAMPLE EMBODIMENTS

Figure 1A:
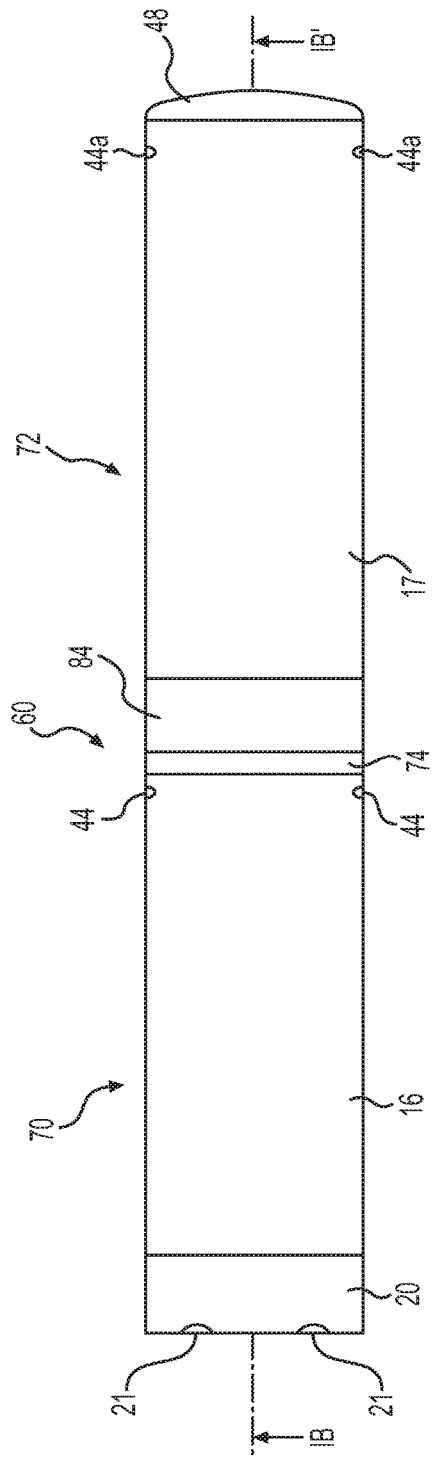
FIG. 1A is a side view of an e-vaping device according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are o cover all modifications, equivalents, and alternatives falling within the scope of example embodiments. Like numbers refer to like elements throughout the description of the figures.

It should be understood that when an element or layer is referred to as being "on," "connected to," "coupled to," or 'covering' another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Figure 1B:
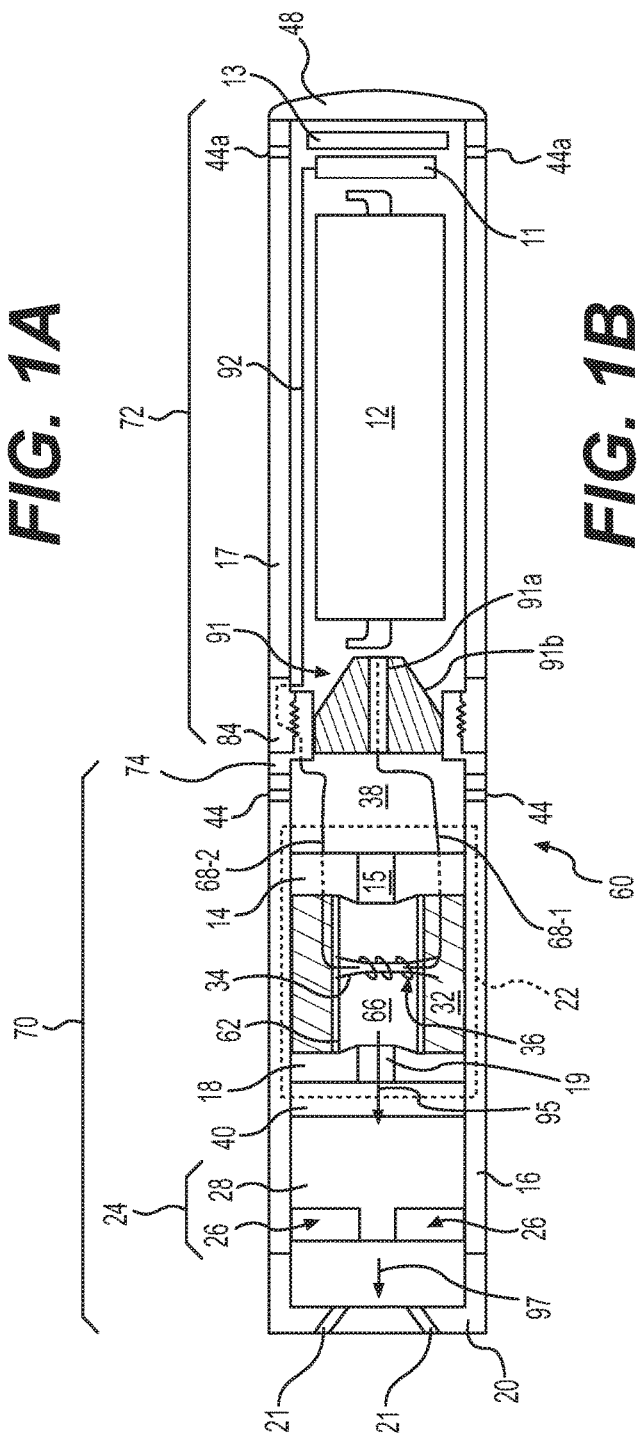
FIG. 1B is a cross-sectional view along line IB-IB' of the e-vaping device of FIG. 1A.

FIG. 1A is a side view of an e-vaping device 60 according to some example embodiments. FIG. 1B is a cross-sectional view along line IB-IB' of the e-vaping device of FIG. 1A. The e-vaping device 60 may include one or more of the features set forth in U.S. Patent Application Publication No. 2013/0192623 to Tucker et al. filed Jan. 31, 2013 and U.S. Patent Application Publication No. 2013/0192619 to Tucker et al. filed Jan. 14, 2013, the entire contents of each of which are incorporated herein by reference thereto. As used herein, the term "e-vaping device" is inclusive of all types of electronic vaping devices, regardless of form, size or shape.

Referring to FIG. 1A and FIG. 1B, an e-vaping device 60 includes a replaceable cartridge (or first section) 70 and a reusable power supply section (or second section) 72. The sections 70, 72 may be coupled together at complimentary interfaces 74, 84 of the respective sections 70, 72.

In some example embodiments, the interfaces 74, 84 are threaded connectors. It should be appreciated that an interface 74, 84 may be any type of connector, including, without limitation, a snug-fit, decent, clamp, bayonet, and/or clasp.

In some example embodiments, one or more of the interfaces 74, 84 include one or more of a cathode connector element and an anode connector element. In the example embodiment illustrated in FIG. 1B, for example, electrical lead 68-2 is coupled to the interface 74. As further shown in FIG. 1B, the power supply section 72 includes a lead 92 that couples the control circuitry 11 to the interface 84. If and/or when interfaces 74, 84 are coupled together, the coupled interfaces 74, 84 may electrically couple leads 68-2 and 92 together.

In some example embodiments, the cartridge 70 includes a connector element 91. Connector element 91 may include one or more of a cathode connector element and an anode connector element. In the example embodiment illustrated in FIG. 1B, for example, electrical lead 68-1 is coupled to the connector element 91. As further shown in FIG. 1B, the connector element 91 is configured to couple with a power supply 12 included in the power supply section 72. If and/or when interfaces 74, 84 are coupled together, the connector element 91 and power supply 12 may be coupled together. Coupling connector element 91 and power supply 12 together may electrically couple leads 68 and power supply 12 together.

The connector element 91 may include an insulating material 91*b* and a conductive material 91*a*. The conductive material 91*a* may electrically couple lead 68-1 to power supply 12, and the insulating material 91*b* may insulate the conductive material 91*a* from the interface 74, such that a probability of an electrical short between the lead 68-1 and the interface 74 is reduced and/or prevented. For example, if and/or when the connector element 91 includes a cylindrical cross-section orthogonal to a longitudinal axis of the e-vaping device 60, the insulating material 91*b* included in connector element 91 may be in an outer annular portion of the connector element 91 and the conductive material 91*a* may be in an inner cylindrical portion of the connector element 91, such that the insulating material 91*b* surrounds the conductive material 91*a* and reduces and/or prevents a probability of an electrical connection between the conductive material 91a and the interface 74.

As shown in FIG. 1A and FIG. 1B, in some example embodiments, an outlet end insert 20 may be positioned at an outlet end of the cartridge 70. The outlet end insert 20 includes at least one outlet port 21 that may be located off-axis from the longitudinal axis of the e-vaping device 60. One or more of the outlet ports 21 may be angled outwardly in relation to the longitudinal axis of the e-vaping device 60. Multiple outlet ports 21 may be uniformly or substantially uniformly distributed about the perimeter of the outlet end insert 20 so as to substantially uniformly distribute vapor drawn through the outlet end insert 20 during vaping. Thus, as a vapor is drawn through the outlet end insert 20, the vapor may move in different directions.

The cartridge 70 includes an outer housing 16 extending in a longitudinal direction and an inner tube 62 coaxially positioned within the outer housing 16. The power supply section 72 includes an outer housing 17 extending in a longitudinal direction. In some example embodiments, the outer housing 16 may be a single tube housing both the cartridge 70 and the power supply section 72 and the entire e-vaping device 60 may be disposable. The outer housing 16 may have a generally cylindrical cross-section. In some example embodiments, the outer housing 16 may have a generally triangular cross-section along one or more of the cartridge 70 and the power supply section 72. In some example embodiments, the outer housing 16 may have a greater circumference or dimensions at a tip end than at an outlet end of the e-vaping device 60.

The cartridge 70 includes a vaporizer assembly 22 and a flavor assembly 24. The vaporizer assembly 22 may form a generated vapor, and the flavor assembly 24 may form a flavored vapor 97 based on elution of one or more flavorants into the generated vapor 95 formed by the vaporizer assembly 22.

The vaporizer assembly 22 may include inner tube 62, gasket 14, gasket 18, a reservoir 32 configured to hold a pre-vapor formulation, a dispensing interface 34 configured to draw pre-vapor formulation from the reservoir 32, and a heater 36 configured to vaporize the drawn pre-vapor formulation.

At one end of the inner tube 62, a nose portion of gasket (or seal) 14 is fitted into an end portion of the inner tube 62. An outer perimeter of the gasket 14 may provide a substantially airtight seal with an interior surface of the outer housing 16. The gasket 14 includes a passage 15 that opens into an interior of the inner tube 62 that defines a channel 66. A space 38 at a backside portion of the gasket 14 assures communication between the passage 15 and one or more air inlet ports 44 located between the gasket 14 and a connector element 91. The connector element 91 may be included in the interface 74.

In some example embodiments, a nose portion of gasket 18 is fitted into another end portion of the inner tube 62. An outer perimeter of the gasket 18 may provide a substantially airtight seal with an interior surface of the outer housing 16. The gasket 18 includes a passage 19 disposed between the channel 66 of the inner tube 62 and the interior of an outlet end insert 20. The passage 19 may transport a vapor from the central channel 66 to the outlet end insert 20 via the flavor assembly 24. In some example embodiments, the vaporizer assembly 22 and the flavor assembly 24 define a space 40 therebetween. The passage 19 may transport the vapor from the central channel 66 to the space 40, from whence the vapor may be drawn in flow communication with the flavor assembly 24 to the outlet end insert 20.

In some example embodiments, at least one air inlet port 44 may be formed in the outer housing 16, adjacent to the interface 74 to minimize the probability of an adult vaper's fingers occluding one of the air inlet ports 44 and to control the resistance-to-draw (RTD) during vaping. In some example embodiments, the air inlet ports 44 may be machined into the outer housing 16 with precision tooling such that their diameters are closely controlled and replicated from one e-vaping device 60 to the next during manufacture.

In some example embodiments, the air inlet ports 44 may be drilled with carbide drill bits or other high-precision tools and/or techniques. In some example embodiments, the outer housing 16 may be formed of metal or metal alloys such that the size and shape of the air inlet ports 44 may not be altered during manufacturing operations, packaging, and vaping. Thus, the air inlet ports 44 may provide consistent RTD. In some example embodiments, the air inlet ports 44 may be sized and configured such that the e-vaping device 60 has a RTD in the range of from about 60 mm $H_2O$ to about 150 mm $H_2O$.

Still referring to FIG. 1A and FIG. 1B, the reservoir 32 may include a pre-vapor formulation. The space defined between the gaskets 14 and 18, the outer housing 16 and the inner tube 62 may establish the confines of the reservoir 32, such that the reservoir 32 may be contained in an outer annulus between the inner tube 62, the outer housing 16 and the gaskets 14 and 18. Thus, the reservoir 32 may at least partially surround the channel 66.

The dispensing interface 34 is coupled to the reservoir 32, such that the dispensing interface 34 may extend transversely across the channel 66 between opposing portions of the reservoir 32. The dispensing interface 34 is configured to draw pre-vapor formulation from the reservoir 32.

The heater 36 is coupled to the dispensing interface 34 and is configured to generate heat. As shown in the example embodiment illustrated in FIG. 1B, the heater 36 may extend transversely across the channel 66 between opposing portions of the reservoir 32. In some example embodiments, the heater 36 may extend parallel to a longitudinal axis of the channel 66.

The dispensing interface 34 is configured to draw pre-vapor formulation from the reservoir 32, such that the pre-vapor formulation may be vaporized from the dispensing interface 34 based on heating of the dispensing interface 34 by the heater 36.

During vaping, pre-vapor formulation may be transferred from the reservoir 32 and/or storage medium in the proximity of the heater 36 via capillary action of a dispensing interface 34. The dispensing interface 34 may include a first end portion and a second end portion. The first and second end portions of the dispensing interface 34 may extend into opposite sides of the reservoir 32. Dispensing interface 34 end portions may be referred to herein as roots. The heater 36 may at least partially surround a central portion of the dispensing interface 34 such that when the heater 36 is activated to generate heat, the pre-vapor formulation in the central portion of the dispensing interface 34 may be vaporized by the heater 36 to form a vapor. The central portion of a dispensing interface 34 may be referred to herein as a trunk.

The reservoir 32 may include a pre-vapor formulation which is free of flavorants, such that when the vaporizer assembly 22 forms a vapor 95, via vaporization of a pre-vapor formulation by the heater 36, the vapor 95 may be substantially absent of flavor, thereby being a "generated vapor." Such an absence of flavorants in the reservoir 32 of the vaporizer assembly 22 may result in mitigation of chemical reactions between pre-vapor formulation materials and the flavorants in the reservoir 32 and upon vaporization as a result of heating of the pre-vapor formulation by the heater 36.

Still referring to FIG. 1A and FIG. 1B, the flavor assembly 24 is positioned between the vaporizer assembly 22 and the outlet end insert 20. The flavor assembly 24 is configured to form a flavored vapor 97 based on elution of a flavorant into a generated vapor 95 formed by the vaporizer assembly 22.

The flavor assembly 24 is positioned in flow communication with both the vaporizer assembly 22, the space 40, and the outlet end insert 20. The cartridge 70 may be configured to direct generated vapors 95 formed by the vaporizer assembly 22 to exit the cartridge 70 via the outlet ports 21. The cartridge 70 may further be configured to direct the generated vapors 95 to pass through space 40 in flow communication with the flavor assembly 24 towards the outlet ports 21. Passing in flow communication with the flavor assembly 24 may include passing through at least a portion of the flavor assembly 24.

The flavor assembly 24 includes at least one flavor material 28 and at least one exposure control mechanism 26. The flavor material 28 holds one or more flavorants. The generated vapor 95 passing through space 40 may act as an eluent, eluting the flavorant from the flavor material 28 and into the generated vapor 95 to form an eluate. The eluate may include the generated vapor 95 and the flavorant. Such an eluate may be referred to as the flavored vapor 97.

The flavor material 28 may be an absorbent material configured to release one or more flavorants into a generated vapor 95 passing through space 40 in flow communication with a surface of the flavor material 28. For example, the flavor material 28 may be a felt material that stores a flavorant absorbed within an internal structure of the felt material. The absorbed flavorant may be released if and/or when a generated vapor 95 passes in flow communication with the absorbent material. For example, the passing generated vapor 95 may elute flavorant from the absorbent material to form the flavored vapor 97.

The flavor material 28 may be a porous structure configured to release one or more flavorants into a generated vapor 95 passing in flow communication with the flavor material 28 through elution. The porous structure may be configured to direct the generated vapor 95 to flow through an internal structure of the porous structure to elute flavorant into the generated vapor 95.

The flavor material 28 may at least partially comprise (e.g., "include") monolithic structure. Such a monolithic structure may be made in a single process step. Such a single process step may include an extrusion of a thermoplastic material laden with flavor (during or post extrusion), molding with or without porous channels within the monolithic structure, some combination thereof, or the like.

In some example embodiments, the flavor material 28 may include one or more materials, including thermoplastic or thermoset material including one or more of polyolefins, polyesters, polyacrylates, polyurethanes, some combination thereof, or the like. In some example embodiments, the flavor material 28 may include a combination of one or more polymers, fillers, additives, some combination thereof, or the like that may be impregnated with one or more flavors. In some example embodiments, the flavor material 28 may include one or more phase change materials. Phase change materials may include one or more of paraffin waxes and fatty acids. In some example embodiments, a generated vapor 95 formed by the vaporizer assembly 22 may have an elevated temperature, relative to the flavor material 28, such that the generated vapor 95 is a "warm" generated vapor 95 relative to the flavor material 28. Phase change materials included in the flavor material 28 may soften or melt as the warm generated vapor 95 from the vaporizer assembly 22 passes in fluid communication therewith, thus promoting flavor elution into the vapor 95 stream. In some example embodiments, the flavor material 28 may be a monolithic material that is a sponge. The sponge may at least partially comprise a cellulose based polymer, a synthetic polymer, some combination thereof, or the like. In some example embodiments, the sponge flavor material 28 is configured to be refilled with one or more flavorants if and/or when the sponge flavor material 28 is depleted or substantially depleted of one or more flavorants.

In some example embodiments, the flavor material 28 may include individual flavor laden particles bound in a monolithic structure that conforms to the holder of the flavor material 28. Flavor laden particles may include one or more of silica, zeolite, activated carbon, inorganic salt type particles, particles made through a granulation process, microcrystalline cellulose spheres, starch based particles, particles made with spray drying encapsulation of flavors ("flavorants"), other types of particles may be impregnated to carry the flavors and may be bound together using a binder to form the structure of the flavor system 28, some combination thereof, or the like.

In some example embodiments, a flavor material 28 may include a gel. The gel may include at least one of a soft and a hard solid gel. A gel may include a natural polymer, synthetic polymer, some combination thereof, or the like that forms gels in aqueous (hydrogel) and/or alcohol (alcogel) systems. The gel may include one or more natural polymers, and such one or more natural polymers may include one or more of carageenan, pullulan, alginates, agar-agar, pectinates, and one or more natural gums. The gel may include one or more synthetic polymers, and such one or more synthetic polymers may include one or more of modified cellulosics, polyacrylates, some combination thereof, or the like. The gel may include one or more salts or pH modifiers configured to promote gelation. The gel may be configured to be affected by the presence of any pH modifiers in the generated vapor 95 that may change its pH, such that the gel is configured to change its gel state as the generated vapor 95 passes over the gel (e.g., in fluid communication therewith) and promote flavor elution into the generated vapor 95 stream. The gel may include one or more dispersed particles that are each laden (e.g., infused, impregnated, etc.) with one or more flavorants.

The exposure control mechanism 26 is configured to adjustably expose the at least one flavor material 28 to the vaporizer assembly 22, such that the elution of flavorant into the generated vapor 95 to form flavored vapor 97 is adjustably controlled. Adjustably controlling flavorant elution to the generated vapor 95 may include adjustably controlling one or more properties of flavor provided by the flavored vapor 97. Such properties may include at least one of a selection of flavorant(s) are included in the flavored vapor 97 and a concentration of said flavorant(s) in the flavored vapor 97.

In some example embodiments, adjustable control of flavored vapor 97 properties may enable a sensory experience provided by the flavored vapor 97 to be controlled. The sensory experience may be controlled to provide an improved sensory experience. For example, the elution of a flavorant may be adjustably controlled to maintain a substantially uniform concentration of flavorant in the flavored vapor 97 as the amount of flavorant and pre-vapor formulation held in the respective flavor assembly 24 and vaporizer assembly 22 are progressively depleted with successive vapings. A substantially uniform concentration of flavorant in the flavored vapor 97 with successive vaping may provide a consistent sensory experience.

In some example embodiments, at least a portion of the exposure control mechanism 26 at least partially extends through one or more apertures (not shown in FIG. 1) in the outer housing 16 such that the exposure control mechanism 26 protrudes to an exterior of the cartridge 70. The portion of the exposure control mechanism 26 may be manually adjusted to adjustably expose the flavor material 28 to the vaporizer assembly 22. As a result, one or more properties of the flavored vapor 97 may be manually controlled by an adult vaper to provide an improved sensory experience according to various adult vaper preferences.

In some example embodiments, the exposure control mechanism 26 includes a drive motor (not shown in FIG. 1) and is coupled to the power supply 12 through one or more electrical links (not shown in FIG. 1). The exposure control mechanism 26 may adjustably expose the flavor material 28 to at least one of the vaporizer assembly 22 and the space 40 based on operation of the drive motor.

Still referring to FIG. 1A and FIG. 1B, the power supply section 72 includes a sensor 13 responsive to air drawn into the power supply section 72 via an air inlet port 44a adjacent to a free end or tip end of the e-vaping device 60, at least one power supply 12, and control circuitry 11. The power supply 12 may include a rechargeable battery. The sensor 13 may be one or more of a pressure sensor, a microelectromechanical system (MEMS) sensor, etc.

In some example embodiments, the power supply 12 includes a battery arranged in the e-vaping device 60 such that the anode is downstream the cathode. A connector element 91 contacts the downstream end of the battery. The heater 36 is coupled to the power supply 12 by at least the two spaced apart electrical leads 68-1 to 68-2.

The power supply 12 may be a Lithium-ion battery or one of its variants, for example a Lithium-ion polymer battery. Alternatively, the power supply 12 may be a nickel-metal hydride battery, a nickel cadmium battery, a lithium-manganese battery, a lithium-cobalt battery or a fuel cell. The e-vaping device 60 may be usable by an adult vapor until the energy in the power supply 12 is depleted or in the case of a lithium polymer battery, a minimum voltage cut-off level is achieved.

Further, the power supply 12 may be rechargeable and may include circuitry configured to allow the battery to be chargeable by an external charging device. To recharge the e-vaping device 60, a Universal Serial Bus (USB) charger or other suitable charger assembly may be used.

Upon completing the connection between the cartridge 70 and the power supply section 72, the at least one power supply 12 may be electrically connected with the heater 36 of the cartridge 70 upon actuation of the sensor 13. Air is drawn primarily into the cartridge 70 through one or more air inlet ports 44. The one or more air inlet ports 44 may be located along the outer housing 16, 17 of the first and second sections 70, 72 or at one or more of the coupled interfaces 74, 84.

The sensor 13 may be configured to sense an air pressure drop and initiate application of voltage from the power supply 12 to the heater 36. As shown in the example embodiment illustrated in FIG. 1B, some example embodiments of the power supply section 72 include a heater activation light 48 configured to glow when the heater 36 is activated. The heater activation light 48 may include a light emitting diode (LED). Moreover, the heater activation light 48 may be arranged to be visible to an adult vaper during vaping. In addition, the heater activation light 48 may be utilized for e-vaping system diagnostics or to indicate that recharging is in progress. The heater activation light 48 may also be configured such that the adult vaper may activate and/or deactivate the heater activation light 48 for privacy. As shown in FIG. 1A and FIG. 1B, the heater activation light 48 may be located on the tip end of the e-vaping device 60. In some example embodiments, the heater activation light 48 may be located on a side portion of the outer housing 17.

In addition, the at least one air inlet port 44a may be located adjacent to the sensor 13, such that the sensor 13 may sense air flow indicative of vapor being drawn through the outlet end of the e-vaping device 60. The sensor 13 may activate the power supply 12 and the heater activation light 48 to indicate that the heater 36 is activated.

In some example embodiments, the control circuitry 11 may control the supply of electrical power to the heater 36 responsive to the sensor 13. In some example embodiments, the control circuitry 11 may include a maximum, time-period limiter. In some example embodiments, the control circuitry 11 may include a manually operable switch for an adult vaper to manually initiate vaping. The time-period of the electric current supply to the heater 36 may be pre-set depending on the amount of pre-vapor formulation desired to be vaporized. In some example embodiments, the control circuitry 11 may control the supply of electrical power to the heater 36 as long as the sensor 13 detects a pressure drop.

In some example embodiments, the control circuitry 11 may control the exposure control mechanism 26 to adjustably control the exposure of the flavor material 28 to the vaporizer assembly 22. The control circuitry 11 may control the supply of electrical power from the power supply 12 to the exposure control mechanism 26 to control the exposure control mechanism 26.

In some example embodiments, the control circuitry 11 may control the exposure control mechanism 26 automatically (e.g., without manual intervention). In some example embodiments, the control circuitry 11 may control the exposure control mechanism 26 based on the amount of generated vapor 95 formed by the vaporizer assembly 22. For example, the amount of flavorant held in the flavor material 28 may decrease in inverse proportion with the amount of generated vapor 95 formed, as flavorants may be progressively eluted into successively formed generated vapors 95.

The control circuitry 11 may control the exposure control mechanism 26 to progressively increase the exposure of the flavor material 28 to the vaporizer assembly 22, so that an increased surface area of the flavor material 28 is exposed as the cumulative amount of generated vapor 95 formed by the vaporizer assembly 22 increases.

Improved exposure of the flavor material 28 to the vaporizer assembly 22 may result in improved flavorant elution from the flavor material 28. For example, as the amount of flavorant held in the flavor material 28 is progressively depleted, the control circuitry 11 may increase the exposure of the flavor material 28 to the vaporizer assembly 22 to maintain a substantially uniform amount of flavorant eluted into the generated vapor 95 during each vaping. As a result, the control circuitry 11 may control the exposure control mechanism 26 to maintain uniform flavorant content in the flavored vapor 97 as the flavor material 28 is progressively depleted of flavorant.

The control circuitry 11 may determine the amount of generated vapor 95 formed by the vaporizer assembly 22 based on at least one of a quantity of vapings supported by the vaporizer assembly 22, a duration of one or more vapings supported by the vaporizer assembly 22, and a cumulative duration of vapings supported by the vaporizer assembly 22.

In some example embodiments, the control circuitry 11 may determine an amount of generated vapor 95 formed based on a lookup table ("LUT") storing associated values of cumulative vaping duration and corresponding values of amounts of generated vapor 95 formed. The associated values included in the LUT may be determined through empirical study. The control circuitry 11 may track a cumulative duration of vapings supported by a vaporizer assembly 22 based on tracking at least one of a quantity of vapings supported by the vaporizer assembly 22 and a duration of one or more vapings supported by the vaporizer assembly 22. The control circuitry 11 may access the LUT and identify a value of an amount of generated vapor 95 that corresponds to the determined cumulative vaping duration in the LUT.

The control circuitry 11 may store, at a storage device, a historical record of at least one of a quantity of vapings supported by the vaporizer assembly 22, a duration of one or more vapings supported by the vaporizer assembly 22, and a cumulative duration of vapings supported by the vaporizer assembly 22. The control circuitry 11 may track the cumulative vaping duration supported by the vaporizer assembly 22 based on updating the historical record according to successive vapings supported by the vaporizer assembly 22.

Still referring to FIG. 1A and FIG. 1B, in some example embodiments, the control circuitry 11 may control the exposure control mechanism 26 based on controlling the supply of electrical power to the exposure control mechanism 26. The control circuitry 11 may control the supply of electrical power such that a particular amount of electrical power is selectively supplied to the exposure control mechanism 26 to cause the exposure control mechanism 26 to implement a particular magnitude of adjustment to the exposure of the flavor material 28.

The control circuitry 11 may control the supply of electrical power to the exposure control mechanism 26 according to a relationship between an amount of electrical power to be supplied to the exposure control mechanism 26 and one or more of the quantity of vapings supported by the vaporizer assembly 22 and the cumulative amount of generated vapor 95 formed by the vaporizer assembly 22. Such a relationship may be stored in a lookup table (LUT). The associated values included in the LUT may be determined through empirical study, where the amounts of electrical power are associated with an amount of adjustment to the exposure of the flavor material 28 to the vaporizer assembly 22 caused by the exposure control mechanism 26. The LUT may be the same as the LUT in which a relationship between quantity and/or duration of vapings and amount of generated vapor 95 formed is stored.

The control circuitry 11 may access the LUT if and/or when the control circuitry 11 determines cumulative amount of generated vapor 95 formed by the vaporizer assembly 22. The control circuitry 11 may identify a corresponding value for an amount of electrical power to be supplied to the exposure control mechanism 26, according to the LUT. The control circuitry 11 may control the supply of electrical power to the exposure control mechanism 26 according to the identified value for the amount of electrical power such that the amount of electrical power is supplied to the exposure control mechanism 26.

To control at least one of the supply of electrical power to a heater 36 and the supply of electrical power to the exposure control mechanism 26, the control circuitry 11 may execute one or more instances of computer-executable program code. The control circuitry 11 may include a processor and a memory. The memory may be a computer-readable storage medium storing computer-executable code.

The control circuitry 11 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 11 may be at least one of an application-specific integrated circuit (ASIC) and an ASIC chip.

The control circuitry 11 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more instances of the control circuitry 11 mentioned above. Examples of program code include both machine code produced by a compiler and higher level program code that is executed using an interpreter.

The control circuitry 11 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The control circuitry 11 may be a special purpose machine configured to execute the computer-executable code to control at least one of the supply of electrical power to the heater 36 and the supply of power to the exposure control mechanism 26. Controlling the supply of electrical power to the heater 36 may be referred to herein interchangeably as activating the heater 36. Controlling the supply of electrical power to the exposure control mechanism 26 may be referred to herein interchangeably as activating the exposure control mechanism 26.

The pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol. The pre-vapor formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

In some example embodiments, the pre-vapor formulation is one or more of propylene glycol, glycerin and combinations thereof.

The pre-vapor formulation may include nicotine or may exclude nicotine. The pre-vapor formulation may include one or more tobacco flavors. The pre-vapor formulation may include one or more flavors which are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

In some example embodiments, a generated vapor 95 formed at the vaporizer assembly 22 may be substantially free of one or more materials being in a gas phase. For example, the generated vapor 95 may include one or more materials substantially in a particulate phase and substantially not in a gas phase.

The storage medium of the reservoir 32 may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section which has a Y-shape, cross shape, clover shape or any other suitable shape. In some example embodiments, the reservoir 32 may include a filled tank lacking any storage medium and containing only pre-vapor formulation.

The reservoir 32 may be sized and configured to hold enough pre-vapor formulation such that the e-vaping device 60 may be configured for vaping for at least about 200 seconds. The e-vaping device 60 may be configured to allow each vaping to last a maximum of about 5 seconds.

The dispensing interface 34 may include a wick. The dispensing interface 34 may include filaments (or threads) having a capacity to draw the pre-vapor formulation. For example, a dispensing interface 34 may be a wick that is be a bundle of glass (or ceramic) filaments, a bundle including a group of windings of glass filaments, etc., all of which arrangements may be capable of drawing pre-vapor formulation via capillary action by interstitial spacings between the filaments. The filaments may be generally aligned in a direction perpendicular (transverse) to the longitudinal direction of the e-vaping device 60. In some example embodiments, the dispensing interface 34 may include one to eight filament strands, each strand comprising a plurality of glass filaments twisted together. The end portions of the dispensing interface 34 may be flexible and foldable into the confines of the reservoir 32. The filaments may have a cross-section that is generally cross-shaped, clover-shaped, Y-shaped, or in any other suitable shape.

The dispensing interface 34 may include any suitable material or combination of materials, also referred to herein as wicking materials. Examples of suitable materials may be, but not limited to, glass, ceramic- or graphite-based materials. The dispensing interface 34 may have any suitable capillary drawing action to accommodate pre-vapor formulations having different physical properties such as density, viscosity, surface tension and vapor pressure.

In some example embodiments, the heater 36 may include a wire coil which at least partially surrounds the dispensing interface 34 in the vaporizer assembly 22. The wire may be a metal wire and/or the wire coil may extend fully or partially along the length of the dispensing interface 34. The wire coil may further extend fully or partially around the circumference of the dispensing interface 34. In some example embodiments, the wire coil may be isolated from direct contact with the dispensing interface 34.

The heater 36 may be formed of any suitable electrically resistive materials. Examples of suitable electrically resistive materials may include, but not limited to, titanium, zirconium, tantalum and metals from the platinum group. Examples of suitable metal alloys include, hut not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heater 36 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heater 36 may include at least one material selected from the group consisting of stainless steel, copper, copper alloys, nickel-chromium alloys, super alloys and combinations thereof. In some example embodiments, the heater 36 may be formed of nickel-chromium alloys or iron-chromium alloys. In some example embodiments, the heater 36 may be a ceramic heater having an electrically resistive layer on an outside surface thereof.

The heater 36 may heat a pre-vapor formulation in the dispensing interface 34 by thermal conduction. Alternatively, heat from the heater 36 may be conducted to the pre-vapor formulation by means of a heat conductive element or the heater 36 may transfer heat to the incoming ambient air that is drawn through the e-vaping device 60 during vaping, which in turn heats the pre-vapor formulation by convection.

It should be appreciated that, instead of using a dispensing interface 34, the vaporizer assembly 22 may include a heater 36 that is a porous material which incorporates a resistance heater formed of a material having a high electrical resistance capable of generating heat quickly.

In some example embodiments, the cartridge 70 may be replaceable. In other words, once one of the flavorant or the pre-vapor formulation of the cartridge 70 is depleted, only the cartridge 70 may be replaced. In some example embodiments, the entire e-vaping device 60 may be disposed once one of the reservoir 32 or the flavor assembly 24 is depleted.

In some example embodiments, the e-vaping device 60 may be about 80 mm to about 110 mm long and about 7 mm to about 8 mm in diameter. For example, in some example embodiments, the e-vaping device 60 may be about 84 mm long and may have a diameter of about 7.8 mm.

As used herein, the term "flavorant" is used to describe a compound or combination of compounds that may provide flavor and/or aroma to an adult vaper. In some example embodiments, a flavorant is configured to interact with at least one adult vaper sensory receptor. A flavorant may be configured to interact with the sensory receptor via at least one of orthonasal stimulation and retronasal stimulation. A flavorant may include one or more volatile flavor substances.

The at least one flavorant may include one or more of a natural flavorant or an artificial ("synthetic") flavorant. The at least one flavorant may include one or more plant extract materials. In some example embodiments, the at least one flavorant is one or more of tobacco flavor, menthol, wintergreen, peppermint, herb flavors, fruit flavors, nut flavors, liquor flavors, and combinations thereof. In some example embodiments, the flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material. In some example embodiments, a flavorant that is a tobacco flavor (a "tobacco flavorant") includes at least one of a synthetic material and a plant extract material. A plant extract material included in a tobacco flavorant may be an extract from one or more tobacco materials.

In some example embodiments, a tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, dark tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

In some example embodiments, the flavorants eluted into the generated vapor 95 are in a particulate phase. A particulate phase may include a liquid phase, solid phase, or the like. In some example embodiments, the flavorants eluted into the generated vapor 95 are in a vapor phase, gas phase, etc. A flavorant may include a volatile flavor substance, and the volatile flavor substance may be eluted into the generated vapor 95. In some example embodiments, a flavorant eluted into the generated vapor 95 includes a nonvolatile flavor substance.

In some example embodiments, if and/or when the flavor assembly 24 holds the flavorant separate from the vaporizer assembly 22 and the cartridge 70 is configured to direct generated vapors 95 through the flavor assembly 24 subsequent to formation of the generated vapor 95, the generated vapor 95 may be cooled from an initial temperature at formation in the vaporizer assembly 22. Where the generated vapor 95 passing through the flavor assembly 24 is cooled from the initial temperature, chemical reactions between the flavorants eluted into the generated vapor 95 and the elements of the generated vapor 95 may be at least partially mitigated, thereby mitigating a loss of desired flavor in the flavored vapor 97.

In some example embodiments, if and/or when the e-vaping device 60 includes a flavor assembly 24 that holds a flavorant separate from the vaporizer assembly 22, the e-vaping device 60 may be configured to mitigate a probability of chemical reactions between the flavorant and one or more elements of the vaporizer assembly 22. An absence of such chemical reactions may result in an absence of reaction products in the flavored vapor 97. Such reaction products may detract from a sensory experience provided by the flavored vapor 97. As a result, an e-vaping device 60 that is configured to mitigate the probability of such chemical reactions may provide a more consistent and improved sensory experience through the flavored vapor 97.

In some example embodiments, a flavor assembly 24 is configured to cool a generated vapor 95 passing through the flavor assembly 24. The flavor assembly 24 may cool a generated vapor 95 based on heat transfer from the generated vapor 95 to at least one of the flavorant eluted into the generated vapor 95 and a material included in the flavor assembly 24. In some example embodiments, the transfer of heat from a generated vapor 95 into at least one of the flavorant and a material included in the flavor assembly 24 increases the amount of flavorant eluted into the generated vapor 95. A flavored vapor 97 having an increased amount of eluted flavorant may provide an improved sensory experience. In some example embodiments, a flavored vapor 97 exiting the flavor assembly 24 may be cooler than a generated vapor 95 entering the flavor assembly 24. A flavored vapor 97 that is cooler than the generated vapor 95 entering the flavor assembly 24 may provide an improved sensory experience based on the reduced temperature of the flavored vapor 97.

In some example embodiments, the flavorants included in an e-vaping device 60 may be replaceable independently of the pre-vapor formulation in the cartridge 70. The flavorants are included in a flavor assembly 24 that is separate from the vaporizer assembly 22 in which the pre-vapor formulation is included. The flavor assembly 24 may be replaced with another flavor assembly 24 to swap the flavorant included in the e-vaping device 60 as desired by an adult vaper. The flavor assembly 24 may be replaced with another flavor assembly 24 to replenish flavorants in the e-vaping device 60 without replacing a vaporizer assembly 22, where the vaporizer assembly 22 may include sufficient pre-vapor formulation to support additional vaping.

Still referring to FIG. 1A and FIG. 1B, when the heater 36 is activated, the activated heater 36 may heat a portion of a dispensing interface 34 surrounded by the heater 36 for less than about 10 seconds. Thus, the power cycle (or maximum vaping length) may range in period from about 2 seconds to about 10 seconds (e.g., about 3 seconds to about 9 seconds, about 4 seconds to about 8 seconds or about 5 seconds to about 7 seconds).

Figure 2C:
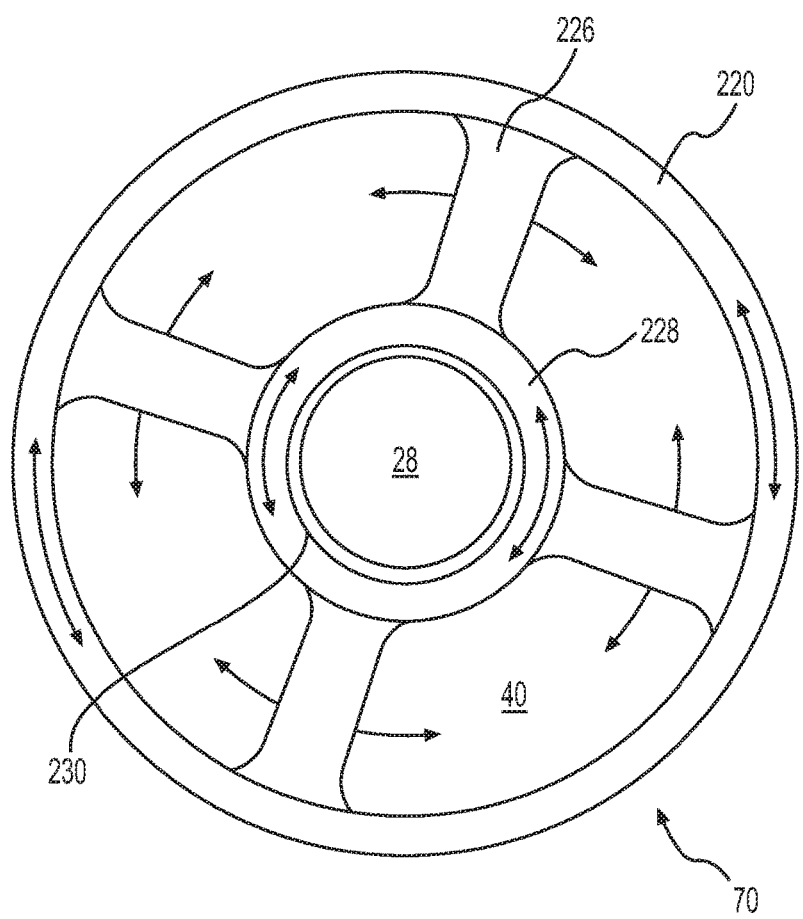
FIG. 2C is a cross-sectional view along line of the flavor assembly of FIG. 2A.

FIG. 2A is a cross-sectional view of a flavor assembly according to some example embodiments. FIG. 2B is a cross-sectional view along line IIB-IIB' of the flavor assembly of FIG. 2A. FIG. 2C is a cross-sectional view along line IIC-IIC' of the flavor assembly of FIG. 2A. The flavor assembly 24 shown in FIG. 2A, FIG. 2B, and FIG. 2C may be included in any of the embodiments included herein, including the flavor assembly 24 shown in FIG. 1B.

In some example embodiments, a flavor assembly 24 includes a flavor material 28 that is in a fixed position, relative to one or more portions of the cartridge 70 in which the flavor assembly 24 is included. As shown in FIG. 2A, FIG. 2B, and FIG. 2C, for example, the flavor assembly 24 is positioned within the space 40 of the cartridge 70, and the flavor assembly 24 includes an exposure control mechanism 26 that is configured to hold the flavor material 28 in a fixed position.

The exposure control mechanism 26 may be configured to adjustably move one or more elements thereof to adjustably expose the flavor material 28 to an exterior environment of the flavor assembly 24. Such exposure may include adjustably exposing the flavor material 28 to a vaporizer assembly 22. In the example embodiment illustrated in FIG. 2A, FIG. 2B, and FIG. 2C, for example, the exposure control mechanism 26 is configured to adjustably expose the flavor material 28 to space 40, where the flavor assembly 24 and the vaporizer assembly 22 are in flow communication through the space 40 as shown in FIG. 1B.

Still referring to FIG. 2A, FIG. 2B, and FIG. 2C, exposure control mechanism 26 includes a fixed (i.e., stationary) structure that includes end gaskets 206a and 206b, fixed ring 230, and sheaths 208a and 208b. End gaskets 206a and 20613 bound opposite ends of the flavor material 28. Fixed ring 230 and fixed sheaths 208a and 208b enclose a portion of the one or more side surfaces of the flavor material 28. The fixed structure partially encloses the flavor material 28 so that the portions of the flavor material 28 that are unenclosed by the support structure are restricted to portions 232a and 232b of the flavor material 28 side surfaces. The unenclosed portions 232a and 232b are at least partially defined by the elements of the fixed structure. For example, the unenclosed portions 232a and 232b are at least partially defined by fixed sheaths 208a and 208b.

In some example embodiments, the exposure control mechanism 26 includes posts 212 that couple fixed structure to an external element to fix at least the flavor material 28 in place relative to the external element. In the example embodiment illustrated in FIG. 2A and FIG. 2C, for example, the exposure control mechanism 26 includes posts 212 that couple end gasket 206b to the outer housing 16 of the cartridge 70, thereby fixing the flavor material 28 and the fixed structure of the exposure control mechanism 26 in place, relative to the outer housing 16 and space 40 included therein.

Still referring to FIG. 2A, FIG. 2B, and FIG. 2C, the exposure control mechanism 26 may be configured to adjustably expose the unenclosed portions 232a and 232b of the flavor material 28 based on adjustably moving the one or more moveable elements. In the example embodiment illustrated in FIG. 2A, FIG. 2B, and FIG. 2C, for example, the exposure control mechanism 26 is configured to adjustably expose the unenclosed portions 232a and 232b of the flavor material 28 to space 40 based on adjustably moving sheaths 222a and 222b.

As shown in FIG. 2A, FIG. 2B, and FIG. 2C, the exposure control mechanism 26 includes a moveable structure that is configured to be rotated around a longitudinal axis 200 of the flavor assembly 24. The moveable structure includes rotatable ring 228, moveable sheaths 222a and 222b, manual interface element 220, and posts 226. The moveable structure is configured to rotate the moveable sheaths 222a and 222b around the longitudinal axis 200 so that the moveable sheaths 222a and 222b may adjustably obscure or expose the unenclosed portions 232a and 232b of the flavor material 28.

As shown in FIG. 2A, FIG. 2B, and FIG. 2C, the moveable structure of the exposure control mechanism 26 includes a rotatable ring 228 to which the moveable sheaths 222a and 222b are coupled. The rotatable ring 228 is configured to rotate around the longitudinal axis 200 to cause the moveable sheaths 222a and 222b to move.

The rotatable ring 228 is coupled to manual interface element 220 through separate posts 226. The manual interface element 220 may be manually manipulated by an adult vaper to cause the rotatable ring 228 to rotate, thus causing the moveable sheaths 222a and 222b to adjustably expose the unenclosed portions 232a and 232b of the flavor material 28 to space 40. Thus, the exposure control mechanism 26 shown in FIG. 2A, FIG. 2B, and FIG. 2C is configured to adjustably expose the flavor material 28 to space 40 based on manual manipulation of the manual interface element 220 of the exposure control mechanism 26.

As shown, the manual interface element 220 and posts 226 may at least partially protrude through one or more apertures in the outer housing 16, such that at least the manual interface element 220 is exposed to an external environment relative to the cartridge 70. Seal elements 224 may substantially seal the gap between the elements of the exposure control mechanism 26 that protrude through the outer housing 16. Substantial sealing of the gap may include sealing the gap such that vapor flow through the gaps is substantially precluded.

In some example embodiments, at least manual interface element 220 and posts 226 may be absent from the flavor assembly 24. For example, the flavor assembly 24 may include a drive motor (not shown in FIG. 2A, FIG. 2B, and FIG. 2C) that is coupled to the rotatable ring 228 such that the flavor assembly 24 is configured to adjustably expose the unenclosed portions 232a and 232b of the flavor material 28 to space 40 based on the drive motor causing the moveable ring to rotate around the longitudinal axis 200.

Figure 3:
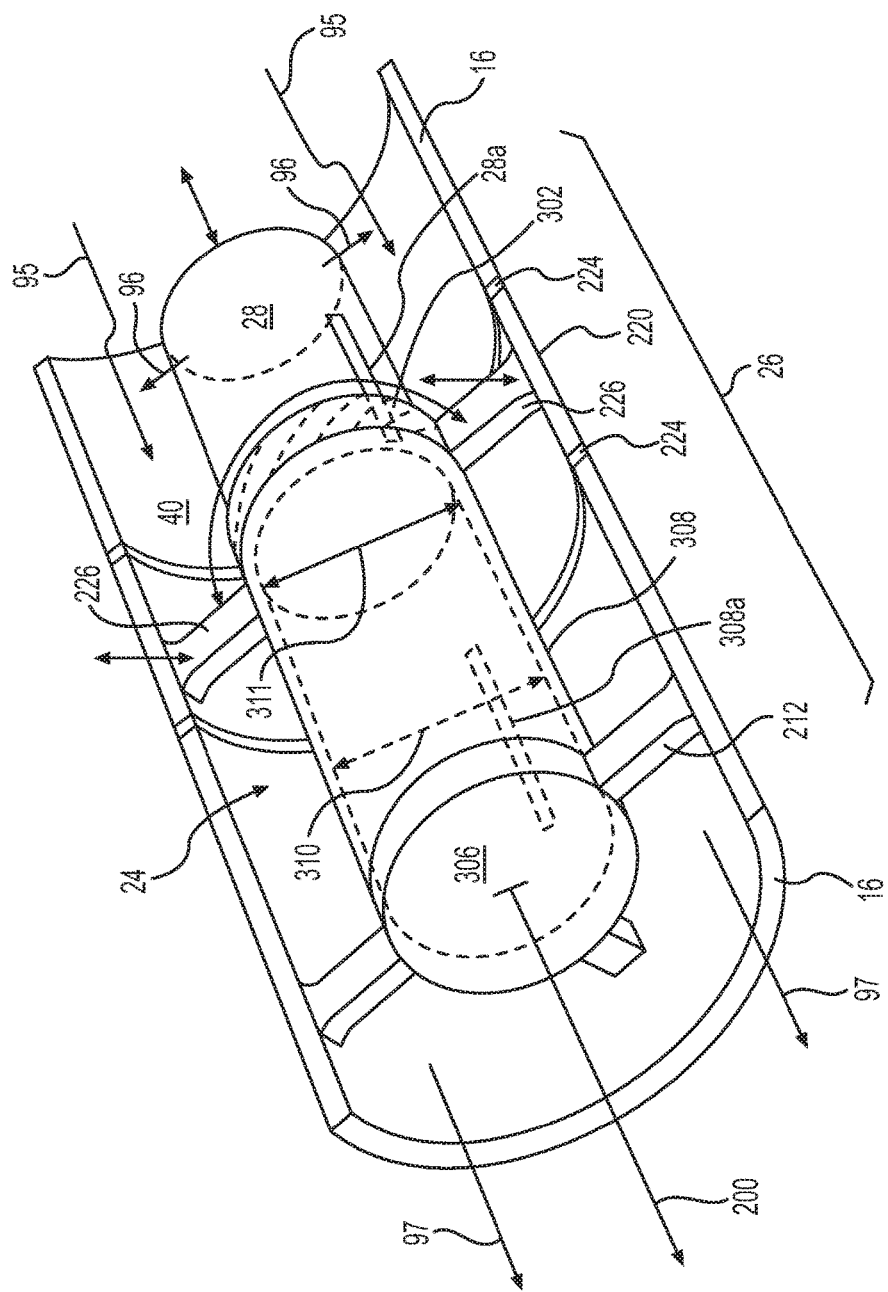
FIG. 3 is a perspective view of a flavor assembly according to some example embodiments.

FIG. 3 is a perspective view of a flavor assembly according to some example embodiments. The flavor assembly 24 shown in FIG. 3 may be included in any of the embodiments included herein, including the flavor assembly 24 shown in FIG. 1B.

In some example embodiments, an exposure control mechanism 26 includes a screw mechanism configured to adjustably translate the flavor material 28 along a longitudinal axis 200 based on the screw mechanism being rotated around the longitudinal axis 200. The screw mechanism may be rotatably adjusted to adjust the translation of the flavor material 28. The translation of the flavor material 28 may include adjustably extending the flavor material 28 from an interior of a sheath configured to isolate the flavor material 28 from at least one of a vaporizer assembly 22 and a space 40 through which generated vapor 95 may pass from the vaporizer assembly 22. The rotation of the screw mechanism may, therefore, adjustably control the exposure of the flavor material 28.

In the example embodiment illustrated in FIG. 3, the flavor assembly 24 includes an exposure control mechanism 26 and a flavor material 28. The exposure control mechanism 26 includes a screw mechanism 302. The screw mechanism 302 is configured to adjustably translate the flavor material 28 along a longitudinal axis 200 based on the screw mechanism 302 rotating around the longitudinal axis 200. As shown in the example embodiments of FIG. 3, the flavor material 28 may include one or more linear guides 28a, and the linear guides may be one or more of a linear trench included in the flavor material 28 and a linear protrusion of the flavor material 28. The linear guide 28 may include a toothed linear protrusion that includes a series of tooth gaps along a linear length of the protrusion. The screw mechanism 302 may include one or more threading elements ("threads") configured to interact ("engage") with one or more linear guides 28 based on rotation of the screw mechanism 302 around axis 200. For example, the threading elements may extend through the toothed gaps in a toothed linear protrusion guide 28a to exert linear force on the linear guide 28a based on rotation of the screw mechanism 302 around axis 200. Based on interaction ("engagement") between the threading elements of the screw mechanism 302 and the one or more linear guides 28a of the flavor material 28, rotational motion of the screw mechanism 302 may be translated into linear motion of the flavor material 28. Thus, the exposure control mechanism 26 is configured to adjustably expose the flavor material 28 to space 40 based on rotation of at least a portion of the exposure control mechanism 26 around a longitudinal axis 200.

In the example embodiment illustrated in FIG. 3, the exposure control mechanism 26 includes a tube 308 and an end gasket 306 that collectively comprise a sheath having an interior space 310. The tube 308 and end gasket 306 define the interior space 310 of the sheath. As shown, the sheath includes an opening 311 at an end distal from the end gasket 306. The sheath is configured to enclose the flavor material 28 within the space 310 such that the flavor material 28 is at least partially isolated from space 40. The exposure control mechanism 26 is configured to adjustably extend the flavor material 28 through the opening 311 of the sheath to be adjustably exposed to space 40 based on rotation of the screw mechanism 302. If and/or when the flavor material 28 is exposed to space 40, flavorant may be eluted 96 from the flavor material 28 into a generated vapor 95 passing through space 40 to form the flavored vapor 97.

As shown, the tube 308 may include a linear guide 308a. The linear guide 308a may be one or more of a linear trench included in the inner surface of the tube 308 and a linear protrusion from the inner surface of the tube 308. The linear guide 308 may be configured to interact with a linear guide 28a of the flavor material 28 to reduce and/or prevent rotational motion of the flavor material 28 based on interaction between the screw mechanism 302 and one or more separate linear guides 28a of the flavor material 28.

For example, if and/or when the linear guide 308a is a linear trench in the inner surface of the tube 308, the linear guide 308a may be configured to receive a linear guide that is a protrusion from the flavor material 28. The protrusion linear guide 28a may slide in the trench linear guide 308a, such that the linear guides 28a, 308a enable linear flavor material 28 motion. The trench linear guide 308a may mitigate movement of the protrusion linear guide 28a out of the trench, thereby mitigating rotational motion of the flavor material 28 around a longitudinal axis 200. Based on reducing and/or preventing rotational motion of the flavor material 28, the linear guide 308a may improve the translation of the rotational motion of the screw mechanism 302 into linear motion of the flavor mechanism 28.

The flavor material 28 may be translated at least partially into the space 310 to isolate the flavor material 28 from the space 40. Isolating the flavor material 28 from the space 40 may at least partially inhibit flavorant elution 96 into generated vapor 95 passing through the space 40, as the flavor material 28 may be isolated from the space 40 by one or more elements of the sheath. As a result, flavorant elution 96 from the flavor material 28 to form the flavored vapor 97 may be adjustably controlled based on adjustably translating the flavor material 28 along longitudinal axis 200 such that the flavor material 28 is adjustably positioned relative to the interior space 310 of the sheath.

In some example embodiments, the screw mechanism 302 is coupled to a manual interface element 220 that may be manually manipulated by an adult vaper to adjustably rotate the screw mechanism 302, thereby adjustably translating the flavor material 28. In the example embodiment illustrated in FIG. 3, for example, the exposure control mechanism 26 includes a manual interface element 220 that is coupled to the screw mechanism 302 through posts 226. The manual interface element 220 at least partially protrudes through one or more gaps in the outer housing 16 such that the manual interface element 220 is exposed to manual manipulation by an adult vaper. Thus, the screw mechanism 302 is configured to rotate based on manually-initiated rotation of the manual interface element 220. The gaps between the outer housing 16 and the manual interface element 220 may be at least partially sealed by one or more seal elements 224.

In some example embodiments, at least manual interface element 220 and posts 226 may be absent from the flavor assembly 24. For example, the flavor assembly 24 may include a drive motor (not shown in FIG. 3) coupled to the screw mechanism 302, such that the screw mechanism 302 is configured to adjustably translate the flavor material 28 along the longitudinal axis 200 based on the drive motor.

In the example embodiment illustrated in FIG. 3, the exposure control mechanism 26 includes one or more posts 212 that fix the sheath to the outer housing 16 and further position the sheath within the space 40 defined by the outer housing 16.

Figure 4B:
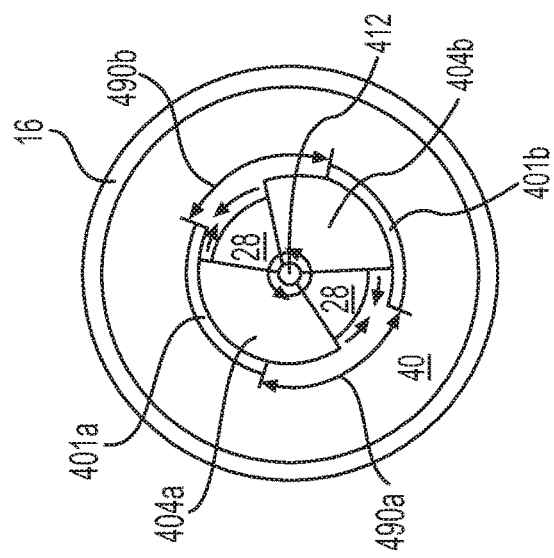
FIG. 4B is a cross-sectional view along line IVB-IVB' of the flavor assembly of FIG. 4A.
Figure 4A:
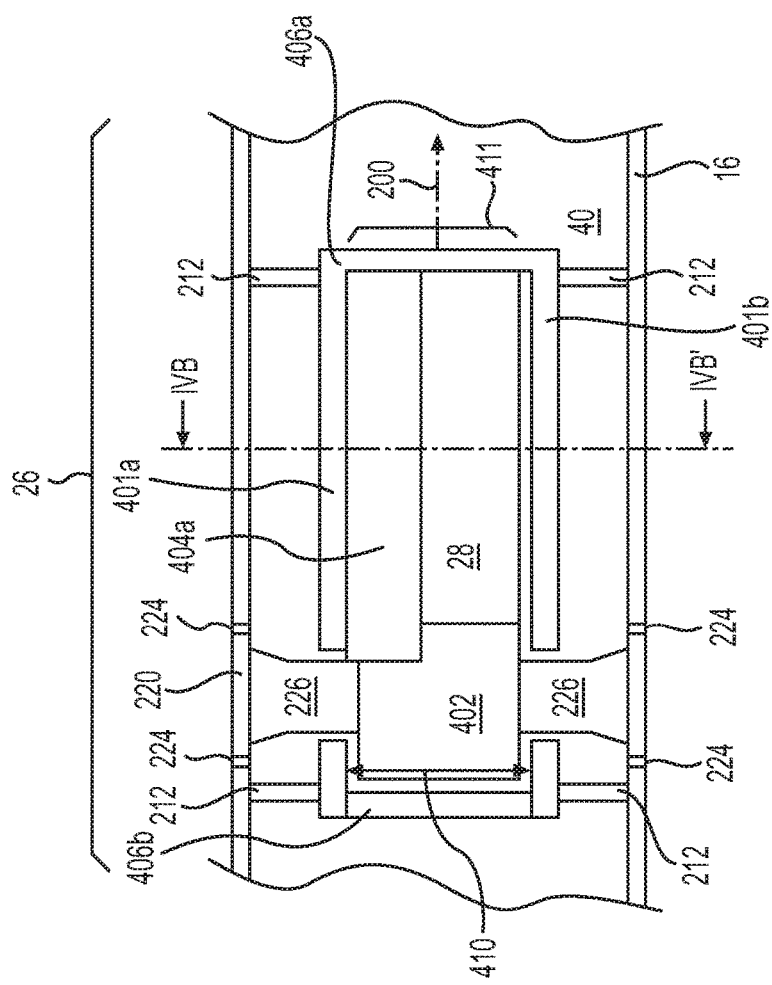
FIG. 4A is a cross-sectional view of a flavor assembly according to some example embodiments.

FIG. 4A is a cross-sectional view of a flavor assembly according to some example embodiments. FIG. 4B is a cross-sectional view along line IVB-IVB' of the flavor assembly of FIG. 4A. The flavor assembly 24 shown in FIG. 4A and FIG. 4B may be included in any of the embodiments included herein, including the flavor assembly 24 shown in FIG. 1B.

In some example embodiments, a flavor assembly 24 includes an exposure control mechanism 26 configured to rotate one or more flavor materials 28 within a fixed sheath structure to adjustably expose the one or more flavor materials 28 to at least one of a vaporizer assembly 22 and a space 40 through which a generated vapor 95 formed by a vaporizer assembly 22 may pass.

Referring to FIG. 4A and FIG. 4B, the exposure control mechanism 26 includes a fixed sheath structure that is coupled to outer housing 16 through posts 212. The fixed structure includes end gaskets 406a and 406b and fixed sheath elements 401a and 401b that collectively define an interior space 410.

As further shown in FIG. 4A and FIG. 4B, the exposure control mechanism 26 includes a rotatable member 411 that is at least partially located within the interior space 410. The rotatable member 411 includes rotatable disc 402, post 412, flavor material 28, and sheath elements 404a and 404b. The rotatable member 411 is configured to be rotated around the longitudinal axis 200. The longitudinal axis 200 may be a central rotational axis of the rotatable member 411. In some example embodiments, the rotatable member 411 may omit one or more of the flavor material 28, rotatable disc 402, post 412, and sheath elements 404a and 404b.

As shown in FIG. 4B, the sheath elements 401a and 401b define gap spaces 490a and 490b between the sheath elements 401a and 401b. The gap spaces 490a and 490b enable fluid communication between the interior space 410 and space 40, thereby enabling flavorant elution from a flavor material 28 included in the interior space 410 to a generated vapor 95 passing through space 40.

In the example embodiment illustrated in FIG. 4A and FIG. 4B, the flavor material 28 may be adjustably exposed to space 40 based on rotation of the rotatable member 411 around the longitudinal axis 200. Based on adjustably exposing the flavor material 28 to the space 40, the elution of flavorant from the flavor material 28 to a generated vapor 95 passing through the space 40 may be adjustably controlled. For example, when the rotatable member 411 is rotated so that the flavor material 28 is isolated from the gap spaces 490a and 490b by one or more of the sheath elements 401a, 401b, 404a, and 404b, flavorant elution between the flavor material 28 and the space 40 may be substantially inhibited.

In the example embodiment illustrated in FIG. 4A and FIG. 4B, the exposure control mechanism 26 includes a manual interface element 220 coupled to the rotatable disc 402 through posts 226. The manual interface element 220 protrudes through the outer housing 16. The gaps between the manual interface element 220 and the outer housing 16 may be sealed with seal elements 224. The sheath elements 401a and 401b may have apertures through which the posts 226 may extend to couple with the rotatable disc 402.

The rotatable member 411 may be adjustably rotated around the longitudinal axis 200 based on manual manipulation of the manual interface element 220. Such manual manipulation may include manually rotating the manual interface element 220 around a longitudinal axis 200 to cause the rotatable member 411 to rotate around the longitudinal axis 200.

In some example embodiments, at least manual interface element 220 and posts 226 may be absent from the flavor assembly 24. For example, the flavor assembly 24 may include a drive motor (not shown in FIG. 4A and FIG. 4B) coupled to at least one of the rotatable disc 402 and the post 412, such that the rotatable member 411 may be adjustably rotated around the longitudinal axis 200 based on the drive motor.

Figure 5:
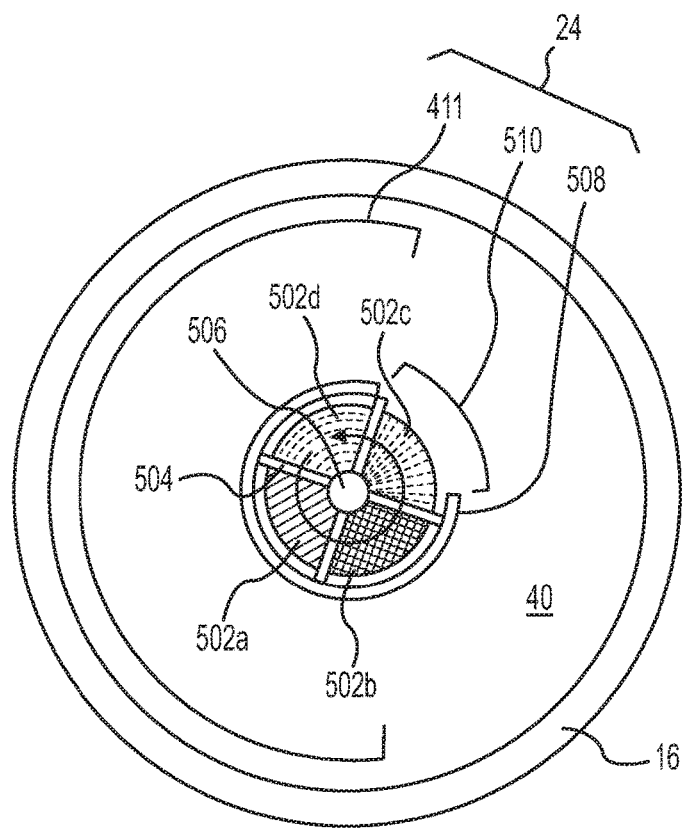
FIG. 5 is a cross-sectional view of a flavor assembly according to some example embodiments.

FIG. 5 is a cross-sectional view of a flavor assembly according to some example embodiments. The flavor assembly 24 shown in FIG. 5 may be included in any of the embodiments included herein, including the flavor assembly 24 shown in FIG. 4A and FIG. 4B.

In some example embodiments, a flavor assembly 24 includes multiple separate flavor materials 28. Two or more of the flavor materials 28 may include separate flavorants. Separate flavor materials 28 may be selectively exposed to a space 40, vaporizer assembly 22, etc. based on adjustable control of an exposure control mechanism 26 coupled to one or more of the flavor materials 28. As a result, flavorant elution into a generated vapor 95 may be selectively controlled.

In the example embodiment illustrated in FIG. 5, for example, a flavor assembly 24 includes a rotatable member 411 that further includes four separate flavor materials 502a, 502b, 502c, and 502d. In some example embodiments, each of the flavor materials 502a, 502b, 502c, and 502d may include a common material configured to hold one or more flavorants. In some example embodiments, two or more of the flavor materials 502a, 502b, 502c, and 502d may include different materials. For example, flavor material 502a may include a felt material and flavor material 502b may include a fibrous wicking material.

Two or more of the flavor materials 502a, 502b, 502c, and 502d may hold different flavorants. For example, each of the flavor materials 502a, 502b, 502c, and 502d may hold a different flavorant.

In the example embodiment shown in FIG. 5, the rotatable member 411 includes a post 506 and partitions 504 that partition adjacent flavor materials 502a, 502b, 502c, and 502d from each other. Where adjacent flavor materials 502a, 502b, 502c, and 502d hold different flavorants, the partitions 504 and post 506 may mitigate pre-vaporization mixing of the different flavorants between adjacent flavor materials.

In the example embodiment illustrated in FIG. 5, the flavor assembly 24 includes a fixed sheath 508 that at least partially encloses the rotatable member 411 and defines a gap space 510 that enables fluid communication between an interior of the fixed sheath and space 40. The rotatable member 411 may be adjustably rotated around a longitudinal axis 200 to adjustably expose one or more of the flavor materials 502a, 502b, 502c, and 502d to the space 40 through the gap space 510. A flavor material 28 may enable flavorant held therein to be eluted into a generated vapor 95 passing through the space 40 based on the flavor material 28 being exposed to the space 40 through the gap space 510.

In some example embodiments, one or more of the partitions 504 and the post 506 may be configured to isolate one or more flavor materials 502a, 502b, 502c, and 502d from the gap space 510 based on a position of the rotatable member 411. In the illustrated example embodiment of FIG. 5, for example, flavor material 502c is exposed to space 40 through the gap space 510, and the partitions 504, post 506, and sheath 508 isolate materials 502a, 502b, and 502d from the space 40.

Based on adjustable rotation of the rotatable member 411, one or more flavor materials 502a, 502b, 502c, and 502d holding one or more particular flavorants may be selectively exposed to space 40 through the gap space 510, thereby configuring the flavor assembly 24 to release a selected flavorant held in the one or more flavor materials 502a, 502b, 502c, and 502d to a generated vapor 95 passing through the space 40.

FIG. 6A is a cross-sectional view of a flavor assembly according to some example embodiments. FIG. 6B is a cross-sectional view along line VIB-VIB' of the flavor assembly of FIG. 6A. The flavor assembly 24 shown in FIG. 6A and FIG. 6B may be included in any of the embodiments included herein, including the flavor assembly 24 shown in FIG. 1B.

In some example embodiments, a flavor assembly 24 may be configured to adjustably translate a flavor material 28 along a longitudinal axis 200 to adjustably expose the flavor material 28 to space 40 based on a lateral force applied in parallel or substantially in parallel with the longitudinal axis 200.

The flavor assembly 24 shown in FIG. 6A and FIG. 6B includes a moveable member 620 that includes a moveable element 608 coupled to the flavor material 28. The moveable member 620 is configured to be adjustably translated along the longitudinal axis 200 based on one or more forces applied to the moveable element 608.

In the illustrated example embodiment of FIG. 6A and FIG. 6B, for example, the flavor assembly 24 is configured to adjustably translate the flavor material 28 along a longitudinal axis 200 based on translation of moveable element 608 along the longitudinal axis 200. The moveable element 608 may be translated along the longitudinal axis 200 based on at least one of a spring force exerted by a spring element 610, a lateral force imparted on moveable element 608 from a manually manipulated manual interface element 220, and a force imparted on the moveable element 608 by a drive motor (not shown in FIG. 6A and FIG. 6B).

In the example embodiment illustrated in FIG. 6A and FIG. 6B, the flavor assembly 24 includes a fixed sheath 601 that is configured to enclose the flavor material 28 within an interior space 602 defined by the fixed sheath 601. The fixed sheath 601 includes a gap space 604 and an opening 630. The flavor assembly 24 is configured to adjustably translate the flavor material 28 along longitudinal axis 200 through the open space 630 to adjustably expose the flavor material 28 to the space 40.

The flavor assembly 24 may include a post 226 that protrudes through the gap space 604 in the fixed sheath 601 and a gap space 624 in the outer housing 16 to couple the moveable element 608 to the manual interface element 220 that is external to the outer housing 16. Based on manual manipulation of the manual interface element 220, the moveable member 620 may be adjustably translated 220a and/or 220b through the interior space 602 to adjustably expose the flavor material 28 to the space 40. In some example embodiments, one or more of the gap spaces 604, 624 may be at least partially sealed by one or more seal elements (not shown in FIG. 6A and FIG. 6B).

In some example embodiments, the flavor assembly 24 includes a spring element 610. The spring element 610 may be configured to exert a spring force on the moveable member 620. The moveable member 620, including the flavor material 28, may be translated along the longitudinal axis 200 based on the spring force exerted by the spring element 610. In some example embodiments, the spring element 610 configured to exert a tension force on the moveable element 608. In some example embodiments, the spring element 610 is configured to exert a compression force on the moveable element 608.

In some example embodiments, the moveable element 608 may be absent from the moveable member 620, such that the moveable member 620 is configured to be adjustably translated along the longitudinal axis 200 based on a force imparted on the flavor material 28. For example, the manual interface element 220 may be coupled to the flavor material 28 through the post 226.

FIG. 7 is a perspective view of a flavor material 28 according to some example embodiments. The flavor material 28 shown in FIG. 7 may be included in any of the embodiments included herein, including the flavor assembly 24 shown in FIG. 1B.

In some example embodiments, at least one flavor material 28 included in a flavor assembly 24 includes a permeation tube that encloses a liquid flavorant. For example, in the example embodiment illustrated in FIG. 7, the flavor material 28 includes a permeation tube 702 and a liquid flavorant 704 enclosed therein.

The permeation tube 702 includes a material that is configured to enable liquid flavorant 704 to permeate from an interior of the permeation tube 702 to an exterior of the permeation tube 702, such that the liquid flavorant 704 may be eluted 96 into a generated vapor 95 passing through space 40 in flow communication with the flavor material 28.

FIG. 8 is a perspective view of a flavor material according to some example embodiments. The flavor material 28 shown in FIG. 8 may be included in any of the embodiments included herein, including the flavor assembly 24 shown in FIG. 1B.

In some example embodiments, a flavor material 28 may include one or more materials that have a high surface area shape. A high surface area shaped material may be a material that includes an increased surface area, relative to a surface area of a cylindrically shaped material having a common internal volume with the high surface area shaped material. A flavor material that has a high surface area shape may be configured to enable improved flavorant elution into a generated vapor, relative to a cylindrical flavor material, based on the increased surface area of the high surface area flavor material.

In some example embodiments, a flavor material that has a high surface area shape may be a helix that extends around a longitudinal axis 200. In the example embodiment illustrated in FIG. 8, for example, the flavor material 28 includes one or more helix-shaped material structures 802-1 to 802-N, where N is a positive integer. As shown in FIG. 8, each of the material structures 802-1 to 802-N is a helix that extends around a common longitudinal axis 200. Each of the material structures 802-1 to 802-N may hold a flavorant. In some example embodiments, two or more of the material structures 802-1 to 802-N may hold different flavorants. Generated vapor 95 may pass in flow communication with one or more of the material structures 802-1 to 802-N. One or more flavorants may be eluted from one or more of the material structures 802-1 to 802-N into the generated vapor 95 to form a flavored vapor 97.

Figure 9:
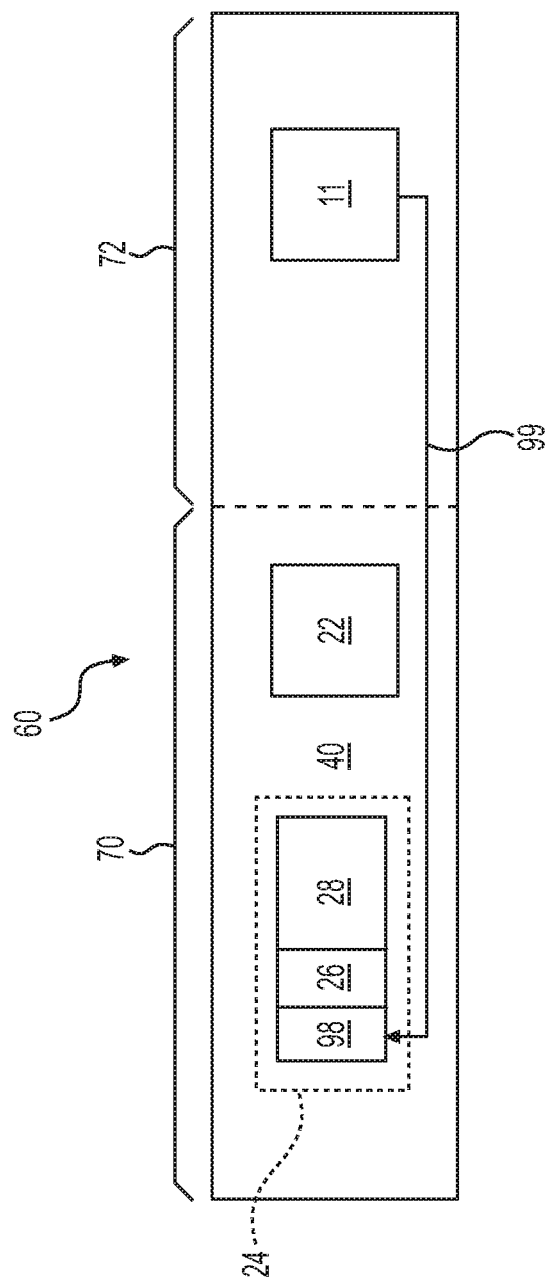
FIG. 9 is a schematic view of an e-vaping device that includes a flavor assembly with a drive motor, according to some example embodiments.

FIG. 9 is a schematic view of an e-vaping device that includes a flavor assembly with a drive motor, according to some example embodiments. The e-vaping device 60 shown in FIG. 1B may be included in any of the embodiments included herein, including the e-vaping device 60 shown in FIG. 1A and FIG. 1B.

In some example embodiments, a flavor assembly 24 includes a drive motor 98 that is coupled to an exposure control mechanism 26. The flavor assembly 24 may be configured to adjustably control the exposure of the flavor material 28 to the vaporizer assembly 22 based on the drive motor 98 adjustably controlling a position of the exposure control mechanism 26.

In some example embodiments, the e-vaping device 60 includes control circuitry 11 that is configured to control the drive motor 98 through a link 99. The link 99 may be at least one of a communication link that communicatively couples the control circuitry 11 to the drive motor 98 and an electrical link that electrically couples the control circuitry 11 to the drive motor 98.

The control circuitry 11 may control the drive motor 98 based on controlling the supply of electrical power to the drive motor 98 through the link 99. The control circuitry 11 may thus adjustably control the exposure of the flavor material 28 to at least one of the vaporizer assembly 22 and space 40 based on controlling the supply of electrical power to the drive motor 98. In some example embodiments, the control circuity 11 may adjustably control the drive motor 98 automatically (e.g., without manual intervention) automatically control the exposure control mechanism 26 to adjustably control the exposure of the flavor material 28 to at least one of the vaporizer assembly 22 and space 40.

Figure 10:
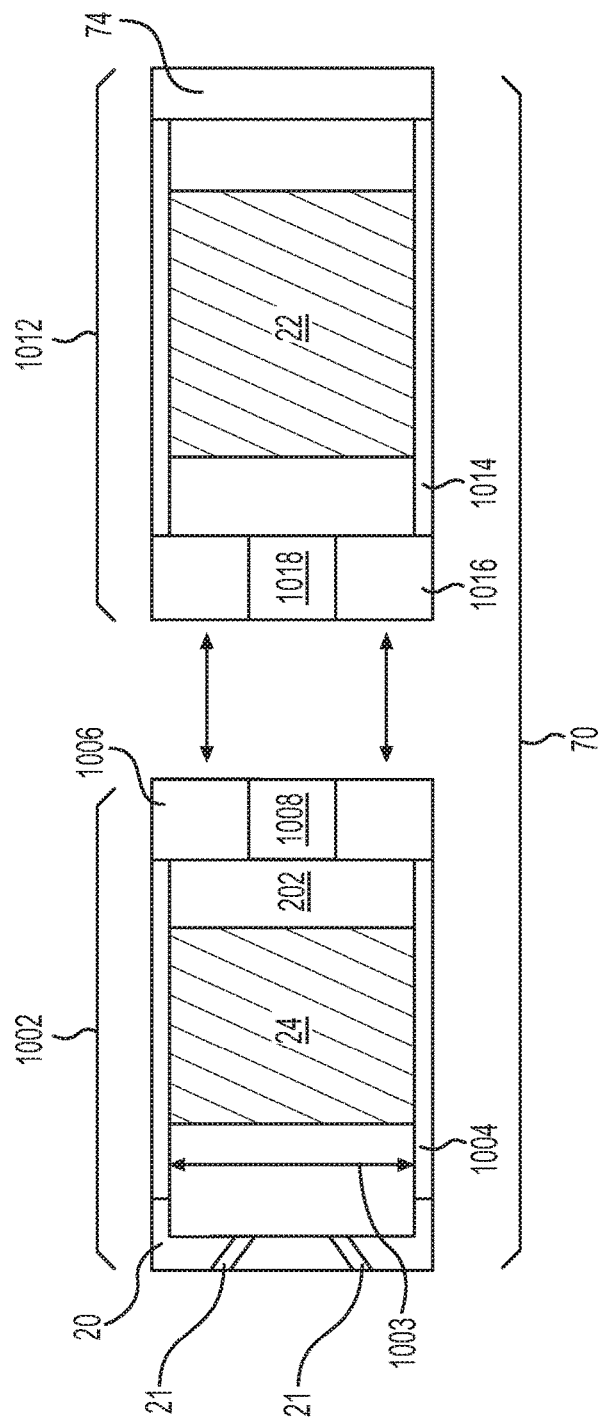
FIG. 10 is a schematic view of a flavor assembly module and a vaporizer assembly module, according to some example embodiments.

FIG. 10 is a schematic view of a flavor assembly module 1002 and a vaporizer assembly module 1012, according to some example embodiments. As shown in FIG. 10, some example embodiments of a cartridge 70 may include the flavor assembly module 1002 and the vaporizer assembly module 1012 coupled together. A cartridge 70 that includes one or more of the flavor assembly module 1002 and the vaporizer assembly module 1012 may be included in any of the embodiments included herein, including the cartridge 70 of the e-vaping device 60 shown in FIG. 1A and FIG. 1B. In some example embodiments, the cartridge 70 shown in FIG.

10 may be coupled with a power supply section 72 illustrated in FIG. 1A and FIG. 1B to form an e-vaping device 60.

In some example embodiments, a cartridge 70 may include multiple modules that may be coupled together to configure the cartridge 70 to provide a flavored vapor 97. The flavor assembly 24 may be included in a flavor assembly module 1002. The flavor assembly module 1002 may be configured to be removably coupled to a vaporizer assembly module 1012. The vaporizer assembly module 1012 may include a vaporizer assembly 22.

As shown in FIG. 10, a cartridge 70 may include a flavor assembly module 1002 and a vaporizer assembly module 1012. Modules 1002, 1012 may be coupled together via complimentary interfaces 1006, 1016. It will be understood that the interfaces 1006, 1016 may include any of the types of interfaces described herein. Each module 1002, 1012 may include a respective housing 1004, 1014.

The vaporizer assembly module 1012 may include a vaporizer assembly 22 within the housing 1014. The vaporizer assembly 22 shown in FIG. 10 may be the vaporizer assembly 22 illustrated in FIG. 1B.

As shown in FIG. 10, the interface 1016 of vaporizer assembly module 1012 may include a conduit 1018, such that the vaporizer assembly 22 held within the housing 1014 of the vaporizer assembly module 1012 is held in flow communication with an exterior of the vaporizer assembly module 1012.

The vaporizer assembly module 1012 may include an interface 74 at one end distal from the interface 1016. The interface 74 may be configured to electrically couple the vaporizer assembly 22 with a power supply 12 included in a separate power supply section 72 of an e-vaping device 60.

The flavor assembly module 1002 may include a flavor assembly 24 within the housing 1004. The flavor assembly 24 shown in FIG. 10 may be the flavor assembly 24 included in any of the example embodiments included herein.

As shown in FIG. 10, the interface 1006 of flavor assembly module 1002 may include a conduit 1008. The conduit 1008 may extend between the interface 1006 and the interior of the housing 1004, such that the flavor assembly 24 held within the housing 1004 of the flavor assembly module 1002 is held in flow communication with an exterior of the flavor assembly module 1002 through the conduit 1008. The interior of the housing 1004 may be referred to herein as a flavor assembly compartment 1003. The flavor assembly module 1002 may include an outlet end insert 20 at an outlet end of the flavor assembly module 1002 and a set of one or more outlet ports 21 in the outlet end insert 20.

In some example embodiments, if and/or when the modules 1002, 1012 are coupled via interfaces 1006, 1016, the modules 1002, 1012 may form a cartridge 70, where the cartridge 70 includes an outlet end insert 20 at an outlet end and an interface 74 at a tip end. The cartridge 70 may further include the flavor assembly 24 being held in flow communication with the vaporizer assembly 22 via coupled conduits 1008, 1018 in coupled interfaces 1006, 1016. The cartridge 70 may further include the flavor assembly 24 being in flow communication with the outlet ports 21, such that generated vapors generated by the vaporizer assembly 22 may pass out of the cartridge 70 by following a pathway extending through the conduits 1018, 1008, and through flavor assembly 24 to the outlet ports 21. The flavor assembly compartment 1003 within the housing 1004 may direct generated vapor 95 received into the flavor assembly compartment 1003 through the conduits 1018, 1008 to pass through the flavor assembly 24.

As shown, the flavor assembly module 1002 may be configured to restrict flow communication through the flavor assembly module 1002 to be through the flavor assembly 24, such that generated vapors passing from the vaporizer assembly 22 to the outlet ports 21 in the formed cartridge 70 are restricted to passing through the flavor assembly 24. The flavor assembly module 1002 housing 1004 may be sized to establish physical contact with the outer surfaces of the flavor assembly 24.

The flavor assembly module 1002 may be configured to be removably coupled with the vaporizer assembly module 1012, so that flavor assembly modules 1002 may be swapped from the vaporizer assembly module 1012.

The flavor assembly module 1002 may be decoupled from the vaporizer assembly module 1012, swapped for a different flavor assembly module 1002, etc. Different flavor assembly modules 1002 may include different flavor assemblies 24, different flavorants, different volatile flavor substances, some combination thereof, etc. Different flavor assemblies 24 may be configured to form different flavored vapors 97 associated with different flavors. As a result, swapping different flavor assembly modules 1002 in a cartridge 70 may enable an adult vaper to swap flavors associated with the flavored vapors 97 provided during vaping independently of swapping entire cartridges 70, thereby improving the sensory experience provided during vaping.

Figure 11:
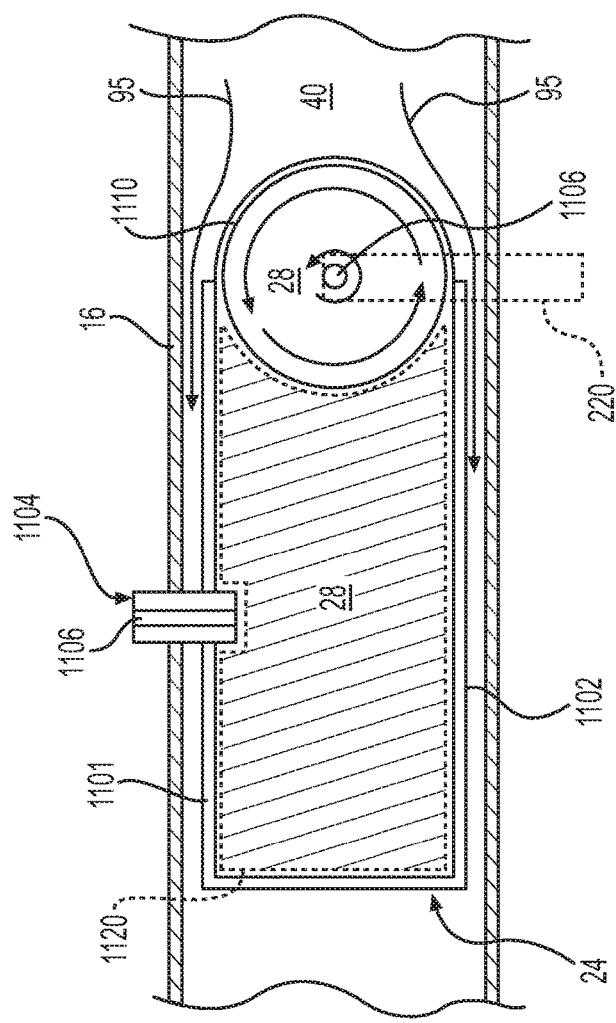
FIG. 11 is a schematic view of a flavor assembly 24 that includes a flavorant reservoir, according to some example embodiments.

FIG. 11 is a schematic view of a flavor assembly 24 that includes a flavorant reservoir, according to some example embodiments.

In some example embodiments, a flavor assembly 24 may include a flavor reservoir 1102. In some example embodiments, one or more portions of a flavor assembly 24 may be configured to be replaced from a cartridge 70. For example, if and/or when the flavor material 28 is a monolithic material, the flavor material 28 may be replaced from the flavor assembly 24 and/or the cartridge 70 if and when the flavor material is depleted or substantially depleted of flavorant. In some example embodiments, the flavorant reservoir 1102 may be configured to be removably installed within the housing 16 of an e-vaping device 60. In some example embodiments, a flavor material 28 included in a flavor assembly 24, including a flavor material 28 included in a reservoir 1102, may be configured to be removably installed in the flavor assembly, such that the flavor material 28 may be replaced if and/or when a flavorant held in the flavor material 28 is depleted or substantially depleted. As shown in FIG. 11, the flavorant reservoir 1102 may include a housing 1101 that at least partially defines an interior reservoir space 1120 in which flavor material 28 may be included. In some example embodiments, the flavor material 28 includes a storage medium configured to hold a flavorant in the reservoir space 1120. In some example embodiments, the flavor material 28 is a liquid flavorant material, such that the flavor material 28 is the flavorant.

In some example embodiments, the reservoir 1102 is configured to be refilled with flavorant, such that the reservoir 1102 is reusable. For example, as shown in FIG. 11, some example embodiments of a reservoir 1102 may include a reservoir interface 1104 that is configured to direct flavorant into the reservoir space 1120. The interface 1104 extends between the reservoir housing 1101 and the outer housing 16 of the cartridge 70, such that the interface 1104 enables fluid communication between the exterior environment and the reservoir space 1120.

As shown in FIG. 11, the interface 1104 may include a conduit 1106 that is configured to direct flavorant from an exterior environment into the reservoir space 1120. The interface 1104 may include a valve assembly (not shown in FIG. 11) that is configured to mitigate a backflow of flavorant from the reservoir space 1120 into the exterior environment through the interface conduit 1106. For example, the interface 1104 may include a check valve assembly.

The interface 1104 may be configured to direct an injection assembly (e.g., injection needle) from an exterior environment into the reservoir 1102 interior space through the conduit, such that flavorant may be introduced (e.g., injected) into the reservoir 1102 interior space via the injection assembly. The interface 1104 may be configured to preclude introduction of elements, including fluids, into the reservoir 1102 without the insertion of an injection assembly through the conduit 1106.

The flavor assembly 24 may include an exposure control mechanism 26 that is configured to adjustably transport at least a portion of the flavorant from the reservoir space 1120 such that the exposure control mechanism 26 adjustably exposes a film 1110 of the flavorant to space 40. For example, in the example embodiments shown in FIG. 11, the exposure control mechanism 26 is a roller element that defines at least a portion of the reservoir space 1120. The roller element may be configured to roll along at least one axis such that a surface of the roller element moves between being exposed to the reservoir space 1120 and being exposed to space 40.

As shown in FIG. 11, some example embodiments of the exposure control mechanism 26 may roll to transport flavorant from the reservoir space 1120 to adjustably expose a film 1110 of flavorant to space 40. The film 1110 of flavorant may be eluted into the vapor 95, and the exposure control mechanism 26 may be rolled to transport additional flavorant to exposure to space 40, thereby replenishing the film 1110.

In some example embodiments, including the example embodiments illustrated in FIG. 11, the exposure control mechanism 26 may be coupled to a manual interface element 220, such that the exposure control mechanism 26 is configured to adjustably expose a portion of flavorant to space 40 based on manual interaction with the manual interface element 220. The manual interface element 220 may be coupled to the exposure control mechanism 26 through one or more linkages. A linkage may include a shaft 1106 illustrated in FIG. 11, where the shaft 1106 couples the roller element exposure control mechanism 26 to a manual interface element 220. The exposure control mechanism 26 may be configured to be adjustably rolled, based on manual interaction with the manual interface element, through the one or more linkages, to transport flavorant from the reservoir 1102 interior to be exposed to space 40 as a film 1110.

In some example embodiments, the exposure control mechanism 26 may be coupled to a drive motor 98 (not shown in FIG. 11). The drive motor 98 may be coupled to the exposure control mechanism 26 through one or more linkages. A linkage may include a shaft 1106 illustrated in FIG. 11, where the shaft 1106 couples the roller element exposure control mechanism 26 to a drive motor 98. The drive motor 98 may be configured to adjustably roll the exposure control mechanism 26, through the one or more linkages, to transport flavorant from the reservoir 1102 interior to be exposed to space 40 as a film 1110.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

I claim:

1. An e-vaping device, comprising:
a cartridge including,
a vaporizer assembly configured to form a generated vapor, and
a flavor assembly coupled to the vaporizer assembly, the flavor assembly configured to mechanically control flavorant elution into the generated vapor to form a flavored vapor, the flavor assembly including
a flavor material holding a flavorant, and
an exposure control mechanism configured to adjustably expose the flavor material to the vaporizer assembly to control elution of the flavorant into the generated vapor;
a power supply section configured to selectively supply power to the vaporizer assembly; and
control circuitry configured to
control the exposure control mechanism to adjustably expose the flavor material to the vaporizer assembly, and
adjustably expose the flavor material to the vaporizer assembly based on a quantity of generated vapor formed by the vaporizer assembly.

2. The e-vaping device of claim 1, wherein
the flavor assembly includes a drive motor coupled to the exposure control mechanism; and
the control circuitry is configured to adjustably control the drive motor to adjustably control the exposure control mechanism based on controlling the drive motor.

3. The e-vaping device of claim 1, wherein the exposure control mechanism is configured to translate the flavor material along a longitudinal axis of the cartridge to adjustably expose the flavor material to the vaporizer assembly.

4. The e-vaping device of claim 3, wherein the exposure control mechanism includes a screw mechanism, the screw mechanism being configured to adjustably translate the flavor material along the longitudinal axis based on rotation of the screw mechanism around the longitudinal axis.

5. The e-vaping device of claim 1, wherein the exposure control mechanism includes a spring element, the spring element being configured to exert a spring force on the flavor material to adjustably expose the flavor material to the vaporizer assembly.

6. The e-vaping device of claim 1, wherein the exposure control mechanism is configured to move a sheath element to adjustably expose the flavor material to the vaporizer assembly.

7. The e-vaping device of claim 6, wherein the exposure control mechanism is configured to rotate the sheath element around a longitudinal axis of the cartridge to adjustably expose the flavor material to the vaporizer assembly.

8. The e-vaping device of claim 1, wherein the flavor material includes a permeation tube enclosing a liquid flavorant, the permeation tube being configured to elute the liquid flavorant to the generated vapor based on permeation of the liquid flavorant through the permeation tube.

9. The e-vaping device of claim 1, wherein the flavor material is a helix extending around a longitudinal axis of the cartridge.

10. The e-vaping device of claim 1, wherein the flavor assembly includes a plurality of flavor materials, at least two of the flavor materials holding different flavorants.

11. The e-vaping device of claim 10, wherein the exposure control mechanism is configured to expose a selected one flavor material of the plurality of flavor materials to the vaporizer assembly.

12. The e-vaping device of claim 1, wherein the flavor material includes a botanical substance, the botanical substance including the flavorant.

* * * * *